US012642828B2

(12) United States Patent
De Simone

(10) Patent No.: US 12,642,828 B2
(45) Date of Patent: Jun. 2, 2026

(54) USE OF BACTERIAL COMPOSITIONS IN THE TREATMENT AND PROPHYLAXIS OF AIRWAY DISEASES

(71) Applicant: Claudio De Simone, Chateau d'Oex (CH)

(72) Inventor: Claudio De Simone, Chateau d'Oex (CH)

(73) Assignee: Claudio De Simone, Chateau d'Oex (CH)

( * ) Notice: Subject to any disclaimer, the term of this patent is extended or adjusted under 35 U.S.C. 154(b) by 403 days.

(21) Appl. No.: 17/913,703

(22) PCT Filed: Feb. 2, 2021

(86) PCT No.: PCT/IB2021/050821
§ 371 (c)(1),
(2) Date: Sep. 22, 2022

(87) PCT Pub. No.: WO2021/209826
PCT Pub. Date: Oct. 21, 2021

(65) Prior Publication Data
US 2023/0113992 A1 Apr. 13, 2023

(30) Foreign Application Priority Data

Apr. 17, 2020 (IT) .......................... 102020000008164

(51) Int. Cl.
*A61K 35/747* (2015.01)
*A61K 9/00* (2006.01)
(Continued)

(52) U.S. Cl.
CPC .......... *A61K 35/747* (2013.01); *A61K 9/0053* (2013.01); *A61K 9/06* (2013.01);
(Continued)

(58) Field of Classification Search
CPC ...... A61K 35/747; A61K 9/0053; A61K 9/06; A61K 35/744; A61K 35/745; A61K 47/02; A61K 47/14; A61K 47/22
See application file for complete search history.

(56) References Cited

U.S. PATENT DOCUMENTS

| | | | |
|---|---|---|---|
| 5,716,615 A * | 2/1998 | Cavaliere Vesely | A23L 29/065 435/252.4 |
| 6,572,854 B1 * | 6/2003 | De Simone | A61P 43/00 435/252.9 |

FOREIGN PATENT DOCUMENTS

WO 2010113595 10/2010

OTHER PUBLICATIONS

Di Marzio, Luisa, et al. "Apoptotic effects of selected strains of lactic acid bacteria on a human T leukemia cell line are associated with bacterial arginine deiminase and/or sphingomyelinase activities." Nutrition and cancer 40.2 (2001): 185-196. (Year: 2001).*

(Continued)

*Primary Examiner* — Louise W Humphrey
*Assistant Examiner* — Candice Lee Swift
(74) *Attorney, Agent, or Firm* — Gregory P. Einhorn; Greer, Burns & Crain, Ltd.

(57) ABSTRACT

The present invention relates to the use of bacterial compositions having an arginine deiminase activity (inhibition of nitric oxide synthase by conversion of L-arginine to L-citrulline) of 1-1,000 μmol L-citrulline/h/g composition and a sphingomyelinase (ceramide generation) activity of 0.01-1.000 nmoles ceramides/h/g composition in the treatment and/or prophylaxis of airway diseases caused by viruses such as influenza viruses, coronaviruses, as SARS-CoV, MERS-CoV and SARS-CoV-2, avian viruses, respiratory syncytial virus (VRS), rhinoviruses, pneumoviruses, or respiratory failure induced or aggravated by viral infections, (Continued)

a b

■ Controls ▨ Patients treated with oral bacteriotherapy angina pectoris, pulmonary heart, respiratory distress, pulmonary edema, neonatal asphyxia, myocardial infarction, heart failure, respiratory failure Pickwick syndrome, pulmonary hypertension, pneumonia or even cystic fibrosis (CF) aggravated by viral infections.

15 Claims, 13 Drawing Sheets

(51) Int. Cl.

| | |
|---|---|
| *A61K 9/06* | (2006.01) |
| *A61K 35/744* | (2015.01) |
| *A61K 35/745* | (2015.01) |
| *A61K 47/02* | (2006.01) |
| *A61K 47/14* | (2017.01) |
| *A61K 47/22* | (2006.01) |
| *A61P 31/14* | (2006.01) |

(52) U.S. Cl.
CPC .......... *A61K 35/744* (2013.01); *A61K 35/745* (2013.01); *A61K 47/02* (2013.01); *A61K 47/14* (2013.01); *A61K 47/22* (2013.01); *A61P 31/14* (2018.01)

(56) References Cited

OTHER PUBLICATIONS

Lucas, Patrick M., et al. "Agmatine deiminase pathway genes in Lactobacillus brevis are linked to the tyrosine decarboxylation operon in a putative acid resistance locus." Microbiology 153.7 (2007): 2221-2230. (Year: 2007).*

Klayraung, Srikanjana, Helmut Viernstein, and Siriporn Okonogi. "Development of tablets containing probiotics: Effects of formulation and processing parameters on bacterial viability." International Journal of Pharmaceutics 370.1-2 (2009): 54-60. (Year: 2009).*

Simonds et al. Health technology assessment (Winchester, England) 14.46 (2010): 131-172. (Year: 2010).*

Rizzardini et al. (British journal of nutrition 107.6 (2012): 876-884 (Year: 2012).*

Rello, Jordi, et al. "High-flow nasal therapy in adults with severe acute respiratory infection: a cohort study in patients with 2009 influenza A/H1N1v." Journal of critical care 27.5 (2012): 434-439. (Year: 2012).*

Waki, N., et al. "Oral administration of Lactobacillus brevis KB290 to mice alleviates clinical symptoms following influenza virus infection." Letters in Applied Microbiology 58.1 (2014): 87-93. (Year: 2014).*

Waki, N., et al. "Effects of probiotic Lactobacillus brevis KB290 on incidence of influenza infection among schoolchildren: an open-label pilot study." Letters in Applied Microbiology 59.6 (2014): 565-571. (Year: 2014).*

Homyak CC, Fernandez A, Touve MA, Zhao B, Anson F, Hardy JA, Vachet RW, Gianneschi NC, Ross JL, Thayumanavan S. Lipogels for Encapsulation of Hydrophilic Proteins and Hydrophobic Small Molecules. Biomacromolecules. Jan. 8, 2018; 19(1):132-140. (Year: 2018).*

D'Ettorre, Gabriella, et al. "Challenges in the management of SARS-CoV2 infection: the role of oral bacteriotherapy as complementary therapeutic strategy to avoid the progression of COVID-19." Frontiers in medicine 7 (2020): 389. (Year: 2020).*

Richards CL, Raffel SJ, Bontemps-Gallo S, Dulebohn DP, Herbert TC, Gherardini FC. Correction: The arginine deaminase system plays distinct roles in Borrelia burgdorferi and Borrelia hermsii. PLoS Pathog. May 10, 2022;18(5):e1010549. (Year: 2022).*

Johns Hopkins; https://www.hopkinsmedicine.org/health/conditions-and-diseases/angina-pectoris; accessed Mar. 11, 2025 (Year: 2025).*

Mayo CLinic; https://www.mayoclinic.org/diseases-conditions/heart-attack/symptoms-causes/syc-20373106; accessed Mar. 11, 2025 (Year: 2025).*

Mayo CLinic 2; https://www.mayoclinic.org/diseases-conditions/pulmonary-edema/symptoms-causes/syc-20377009; accessed Mar. 11, 2025 (Year: 2025).*

NCBI; https://www.ncbi.nlm.nih.gov/datasets/gene/GCF_000359625.1/?search=deiminase; accessed Mar. 13, 2025 (Year: 2025).*

Soudani, Nadia, et al. "Ceramide suppresses influenza A virus replication in vitro." Journal of Virology 93.7 (2019): 10-1128. (Year: 2019).*

Akaike, T., and H. Maeda. "Nitric oxide and virus infection." Immunology 101.3 (2000): 300-308. (Year: 2000).*

Perrone, Lucy A., et al. "Inducible nitric oxide contributes to viral pathogenesis following highly pathogenic influenza virus infection in mice." The Journal of infectious diseases 207.10 (2013): 1576-1584. (Year: 2013).*

Chen, Luni, et al. "Inhalation of nitric oxide in the treatment of severe acute respiratory syndrome: a rescue trial in Beijing." Clinical infectious diseases 39.10 (2004): 1531-1535. (Year: 2004).*

Prakash, Hridayesh, et al. "Ceramide-1 Phosphate: Multi-targets Immune Adjuvant for Controlling Covid-19 infection?." (2020)., Apr. 13, 2020 preprint from https://osf.io/preprints/osf/nfdsc; accessed May 30, 2025 (Year: 2020).*

Kumar, Sandeep, et al. "Sphingolipid Biosynthesis Inhibition as a Host Strategy Against Diverse Pathogens." bioRxiv (2020): Apr. 2020. (Year: 2020).*

Ögel, Zümrüt Begüm, and Hale İnci Öztürk. "Antiviral mechanisms related to lactic acid bacteria and fermented food products." Biotech Studies 29.1 (2020): 18-28. (Year: 2020).*

Infusino, Fabio, et al. "Diet supplementation, probiotics, and nutraceuticals in SARS-CoV-2 infection: a scoping review." Nutrients 12.6 (2020): 1718. (Year: 2020).*

Sundararaman, Aravind, et al. "Role of probiotics to combat viral infections with emphasis on COVID-19." Applied microbiology and biotechnology 104.19 (2020): 8089-8104. (Year: 2020).*

Bottari, Benedetta, Vincenzo Castellone, and Erasmo Neviani. "Probiotics and COVID-19." International journal of food sciences and nutrition 72.3 (2021): 293-299. (Year: 2020).*

Castelli, Vanessa, et al. "Effects of the probiotic formulation SLAB51 in in vitro and in vivo Parkinson's disease models." Aging (albany NY) 12.5 (2020): 4641. (Year: 2020).*

Q Hao, "Probiotics for preventing acute upper respiratory tract infections", Feb. 3, 2015 (Feb. 3, 2015), http://www.hcbi.nlm.nih.gov/pubmed/25927096.

Min-Kyung Park et al, "Lactobacillus plantarum DK119 as a Probiotic Confers Protection against Influenza Virus by Modulating Innate Immunity", PLOS ONE,vol. 8, No. 10, Oct. 4, 2013 (Oct. 4, 2013).

N. Waki et al, "Effects of probiotic Lactobacillus brevis KB290 on incidence of influenza infection among schoolchildren: an open-label pilot study", Letters in Applied Microbiology, vol. 59, No. 6, Oct. 30, 2014 (Oct. 30, 2014), p. 565-571.

Gabriella D'Ettorre et al, "Challenges in the Management of SARS-CoV2 Infection: The Role of Oral Bacteriotherapy as Complementary Therapeutic Strategy to Avoid the Progression of COVID-19", Frontiers in Medicine, vol. 7, Jul. 7, 2020.

Stefania Perrucci et al, "In vitro and ex vivo evaluation of the anti-Giardia duodenalis activity of the supernatant of Slab51 (SivoMixx)", PLOS ONE,vol. 14, No. 3, Jan. 1, 2019.

Vasquez Elisardo C. et al, "Probiotics as Beneficial Dietary Supplements to Prevent and Treat Cardiovascular Diseases: Uncovering Their Impact on Oxidative Stress", US May 7, 2019 (May 7, 2019), vol. 2019, p. 1-11.

Lehtoranta L et al, "Probiotics in respiratory virus infections", Mar. 18, 2014 (Mar. 18, 2014), vol. 33, No. 8, p. 1289-1302.

Fan Qiong-Li et al, "Synbiotics for prevention of ventilator-associated pneumonia: a probiotics strain-specific network meta-analysis", GB Nov. 1, 2019 (Nov. 1, 2019), vol. 47, No. 11, p. 5349-5374.

* cited by examiner

USE OF BACTERIAL COMPOSITIONS IN THE TREATMENT AND PROPHYLAXIS OF AIRWAY DISEASES

RELATED APPLICATIONS

This application is a national phase application claiming benefit of priority under 35 U.S.C. § 371 to Patent Convention Treaty (PCT) International Application serial number PCT/IB2021/050821, filed Feb. 2, 2021, now pending, which claims the benefit of priority to Italian patent No. 102020000008164, filed on Apr. 17, 2020. The aforementioned applications are expressly incorporated herein by reference in their entirety and for all purposes.

FIELD OF THE INVENTION

The present invention relates to the use of bacterial compositions having an arginine deiminase activity (inhibition of nitric oxide synthase by conversion of L-arginine to L-citrulline) of 1-1,000 µmol L-citrulline/h/g composition and a sphingomyelinase (ceramide generation) activity of 0.01-1.000 nmoles ceramides/h/g composition in the treatment and/or prophylaxis of airway diseases caused by viruses such as influenza viruses, coronaviruses, as SARS-CoV, MERS-CoV and SARS-CoV-2, avian viruses, respiratory syncytial virus (VRS), rhinoviruses, pneumoviruses, or respiratory failure induced or aggravated by viral infections, angina pectoris, pulmonary heart, respiratory distress, pulmonary edema, neonatal asphyxia, myocardial infarction, heart failure, respiratory failure Pickwick syndrome, pulmonary hypertension, pneumonia or even cystic fibrosis (CF) aggravated by viral infections.

BACKGROUND OF THE INVENTION

It has been observed recently, that coronavirus disease 2019 (COVID-19), similar to that caused by SARS-CoV, is characterized by an excessive inflammatory response induced by a cytokine storm associated with disease severity (Huang, C. et al., 2020; Peiris, J S M. et al., 2003). Patients requiring intensive care unit (ICU) have higher plasma levels of many cytokines such as IP-10, MCP-1, MIP-1A, and TNF-α than non-ICU subjects (Prompetchara, E. et al., 2020), suggesting a likely involvement of a pro-inflammatory condition in disease progression and severity. Furthermore, in the lungs of patients with severe manifestations of COVID-19, a high infiltration of inflammatory cells has been observed (Xu, Z. et al., 2020; Tian, S. et al., 2020). These aberrant pathogenic cells together with inflammatory monocytes can enter the pulmonary circulation playing a detrimental role in immune responses, causing pulmonary functional disabilities resulting in hypoxemia, organ damage, and rapid mortality.

The activity of enzymes and metabolites produced by bacteria belonging to the genus *Lactobacillus, Bifidobacterium* and *Streptococcus* is the basis of the action that these microorganisms can play against viral infections. In this context, a considerable interest is aroused by the production of the bacterial enzymes sphingomyelinase (SMase) (Lew, L C. and Liong, M T., 2013) and arginine deiminase (ADI) (Cunin, R. et al., 1986) able to catalyze the formation of ceramides similar to those present in the membranes of eukaryotic cells and to modulate the production of nitric oxide through competitive inhibition of nitric oxide synthase 2 (NOS2) respectively.

Regarding SMase activity, ceramides produced by the catalytic activity of this enzyme, through a series of signaling cascades, play crucial roles in distinct physiological processes, including cell membrane remodeling, migration, proliferation, differentiation, and cell death. Several studies highlight that ceramides are able to inhibit the replication of different viruses, including those responsible for influenza (Tian, Y. et al., 2019), suggesting that manipulating the metabolism of such biological macromolecules may represent a therapeutic approach to counter viral infections (Dai, L. et al., 2015, Finnegan, C M. et al., 2004; Darwiche, N. et al., 2005; Pritzl, C J. et al., 2015). Recently, it has been reported that sphingomyelinase enzymatic activity would be associated with an increased ability of SARS-CoV-2 virus to infect and propagate within susceptible human cells. Mechanistically, acidic sphingomyelinase would be responsible for the formation of ceramide-enriched membranous platforms prone to viral infection mediated by the spike protein (Carpinteiro et al., 2020; Schloer et al., 2020). Inhibition of this enzyme would be associated with a reduced risk of SARS-CoV-2 infections.

Nitric oxide (NO) represents a potent signaling molecule synthesized by many human cell types. It also regulates the functional activity, proliferation, and death of many immune and inflammatory cell types including macrophages, T lymphocytes, and neutrophils. Inducible nitroxide synthase 2 (NOS2) constitutes the major enzyme involved in high levels of NO synthesis (Green, S J. et al., 1994; Bhat, N R. et al., 1999). Systemic inhibition of NO and subsequent modulation of the inflammatory response has been reported as a protective factor against inauspicious events related to viral infections (Perrone, LA. et al., 2012; Akaike, T. et al., 1996). Although with conflicting results in relation to different diseases of viral origin, the treatment with nitric oxide (NO) has been reported to have an apparent beneficial action against SARS-CoV infections (Chen, R. et al., 2004; Darwish, I. et al., 2009). Recently, it has been proposed that NO administration may be effectively used in the treatment of COVID-19 patients on the base of the antiviral activity shown by this molecule, as well as, the central role played by NO in modulating the immune response and preventing the cytokine storm characteristic of SARS-CoV-2 infections (Adusumilli, NC. et al., 2020).

In contrast to hypotheses indicating the inhibition of sphingomyelinase activity and NO delivery as possible treatments for COVID-19 patients, the Applicant has now surprisingly found that oral administration, directly into the airway or rectally, of specific bacterial compositions containing bacteria rich in sphingomyelinase and arginine deiminase, inhibiting nitroxide production, can improve the oxygenation, the antiviral and immune response of subjects who have hypoxia and/or hypoxemia, whether or not associated with infections.

Compendium of Invention

An object of the present invention is the use of bacterial compositions having an arginine deiminase activity (inhibition of nitric oxide synthase by conversion of L-arginine to L-citrulline) of 1-1,000 µmol L-citrulline/h/g composition and a sphingomyelinase (ceramide generation) activity of 0.01-1.000 nmoles ceramides/h/g composition in the treatment and/or prophylaxis of airway diseases caused by viruses such as influenza viruses, coronaviruses, as SARS-CoV, MERS-CoV and SARS-CoV-2, avian viruses, respiratory syncytial virus (VRS), rhinoviruses, pneumoviruses, or respiratory failure induced or aggravated by viral infections, angina pectoris, pulmonary heart, respiratory distress, pulmonary edema, neonatal asphyxia, myocardial infarction, heart failure, respiratory failure Pickwick syndrome, pulmonary hypertension, pneumonia or even cystic fibrosis (CF) aggravated by viral infections.

A further object of the invention relates to the above mentioned use, wherein the bacterial compositions comprise one or more strains of the species *Lactobacillus brevis* and *Lactobacillus plantarum*.

A further object of the invention relates to the above mentioned use, wherein the bacterial compositions comprise 99.99% to 0.01% of one or more strains of the species *Lactobacillus brevis* and *Lactobacillus plantarum* and optionally at least one pharmaceutically acceptable excipient.

A further object of the invention relates to the above mentioned use wherein, in addition to *Lactobacillus brevis* and *Lactobacillus plantarum*, the bacterial compositions comprise one or more strains of the species chosen from *Lactobacillus paracasei, Lactobacillus acidophilus, Lactobacillus helveticus, Streptococcus thermophilus* and/or *Bifidobacterium animalis* subsp. *lactis* and possibly at least one pharmaceutically acceptable excipient.

A further object of the invention relates to the above mentioned use, wherein the compositions comprise from 1% to 70% by weight of *Lactobacillus brevis*, from 1% to 30% by weight of *Lactobacillus plantarum*, from 1% to 20% by weight of *Lactobacillus paracasei*, 1% to 20% by weight of *Lactobacillus acidophilus*, 1% to 20% by weight of *Lactobacillus helveticus*, 1% to 70% by weight of *Streptococcus thermophilus*, and 1% to 40% by weight of *Bifidobacterium animalis* subsp. *lactis*, and possibly at least one pharmaceutically acceptable excipient.

A further object of the invention relates to the above mentioned use, wherein the compositions are suitable for oral administration, such as in the form of powders, capsules, granules or lipogels.

A further object of the invention relates to the above mentioned use, wherein the oral compositions have a high concentration of bacteria, to the extent of 50 billion to 8,000 billion.

A further object of the invention relates to the above mentioned use, wherein the compositions are suitable for insertion into and use in conjunction with facial masks or Non Invasive Ventilation (NIV) devices.

A further object of the invention relates to the above mentioned use, wherein the compositions are suitable for administration via the airways, such as by inhalation, insufflation or in the form of a powder, solution, suspension or dispersion spray or aerosol fluid, or nasal drops, preferably as an aerosol fluid.

A further object of the present invention relates to the above use, wherein the administration is in the form of a fluid or powder by aerosol or insufflation, comprising at least 0.001% by weight of *Lactobacillus brevis* and at least 0.001% by weight of *Lactobacillus plantarum* and saline or purified water.

A further object of the present invention relates to the above use, wherein the administration is in the form of a fluid or powder by aerosol or insufflation, comprising from 1% to 70% by weight of *Lactobacillus brevis*, from 1% to 30% by weight of *Lactobacillus plantarum*, 1% to 20% by weight of *Lactobacillus paracasei*, 1% to 20% by weight of *Lactobacillus acidophilus*, 1% to 20% by weight of *Lactobacillus helveticus*, 1% to 70% by weight of *Streptococcus thermophilus*, and 1% to 40% by weight of *Bifidobacterium animalis* subsp. *lactis*, and saline or purified water.

A further object of the present invention relates to the above use, wherein the aerosol or insufflation fluid or powder compositions have a high concentration of bacteria, to the extent of 100,000 to 50 billion.

A further object of the present invention relates to the use of the above in the form of lipogels for oral, buccal or rectal use, preferably rectal, in which the compositions have a high concentration of bacteria, to the extent of 1 billion to 800 billion per gram.

A further object of the present invention relates to the above use, wherein the compositions are used in combination with further treatments, in particular with an oxygen therapy or ozone therapy treatment.

A further object of the present invention relates to the above use, wherein the bacteria used in the compositions of the present invention are viable, non-viable, sonicated, tindalized or lyophilized.

A composition of the invention makes it possible to achieve an increase in anti-inflammatory activity, as measured by determining the respiratory or systemic inflammation value [erythrocyte sedimentation rate (ESR), C-reactive protein (CRP), procalcitonin (PCT), D-dimer, or ferritin], of at least 30% compared to an equal control composition. The composition also allows for antagonizing reductions in oxygen detectable in arterial blood or capillaries, and thereby improving hypoxemia, hypoxia, and/or organ and tissue functionalities.

The compositions of the invention may be prepared according to methods known in the art.

BRIEF DESCRIPTION OF DESIGNS

FIG. 1 shows the formation of NO catalyzed by NOS.

Figure 5:
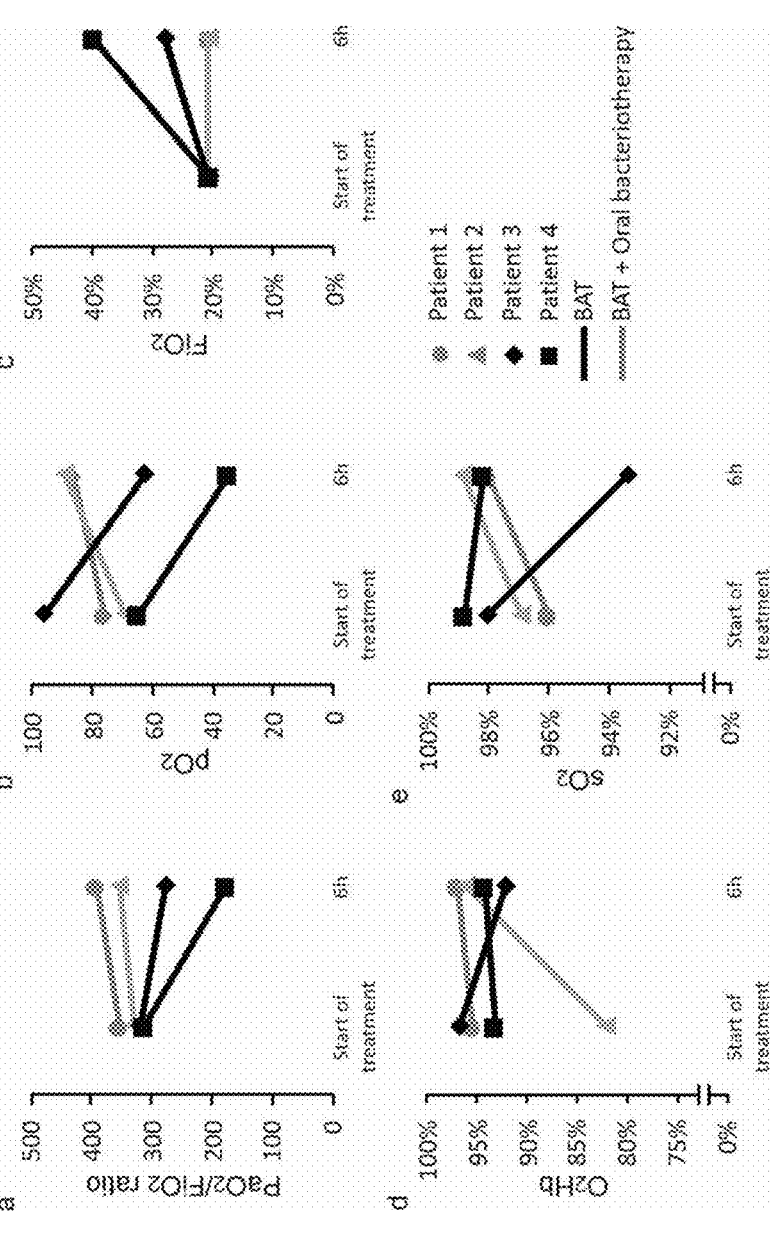

FIG. 5 shows the trend at 6 hours after the start of treatment of oxygenation parameters: a) $PaO_2/FiO_2$ ratio, b) blood partial pressure of oxygen ($pO_2$), c) fraction of inspired oxygen ($FiO_2$), d) oxygenated hemoglobin ($O_2Hb$), and e) oxygen saturation ($sO_2$) for a representative group of patients treated with best available therapy (BAT) and subjects additionally supplemented with oral bacteriotherapy.

Figure 6:
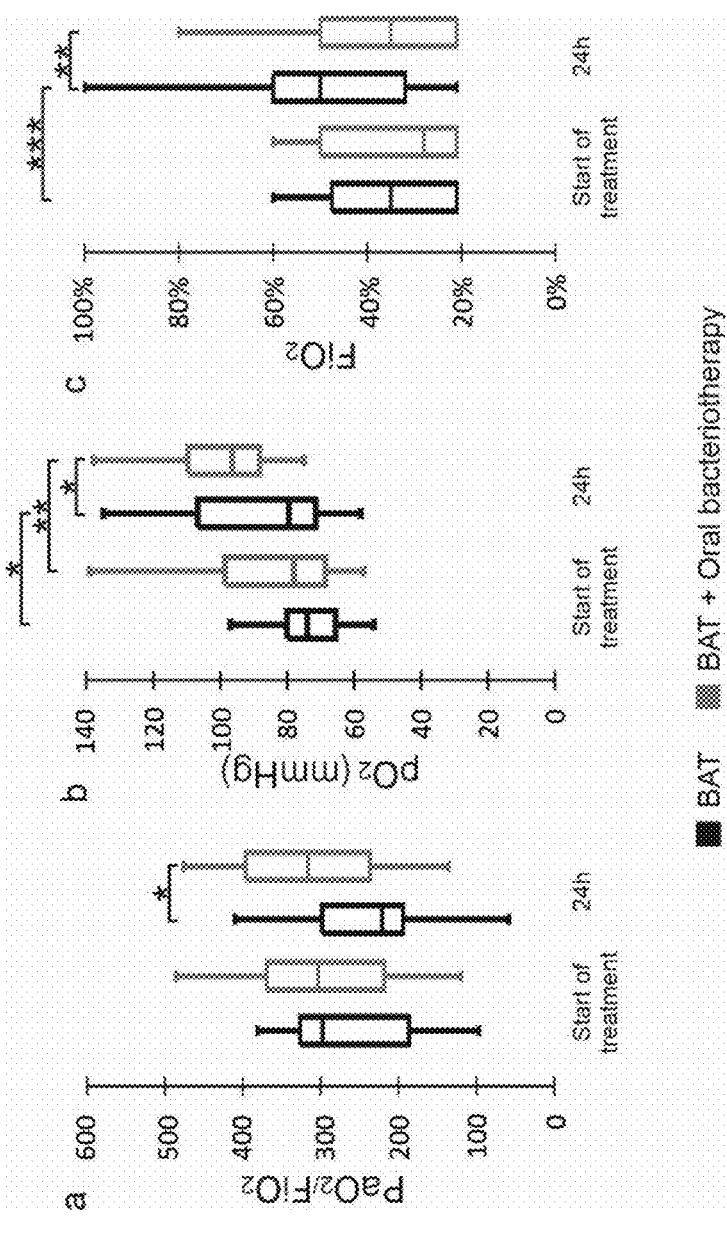

FIG. 6 shows box and whisker plots relative to the distribution of values of (a) $PaO_2/FiO_2$ ratio, (b) blood partial pressure of oxygen ($pO_2$), and (c) inspired oxygen fraction ($FiO_2$) within the group treated with oral bacteriotherapy and the group treated with the best available therapy (BAT) for COVID-19 at the beginning of treatment and after 24 hours. Where present, statistical significance between the two groups at each considered time point and, for each group, between consecutive time points was reported.

Figure 7:
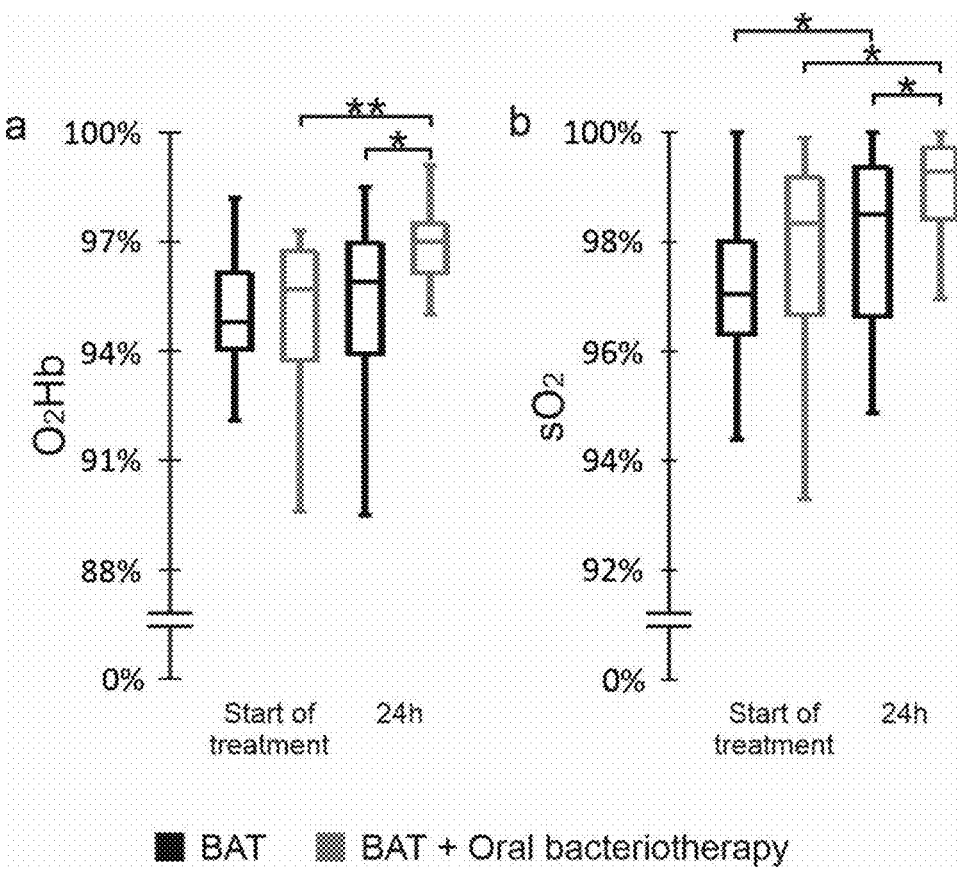

FIG. 7 shows box and whisker plots describing the distribution of the values of (a) oxygenated hemoglobin ($O_2Hb$) and (b) percentage of oxygenated and oxygen-saturated hemoglobin ($sO_2$) within the group treated with oral bacteriotherapy and the group treated with the best available therapy (BAT) for COVID-19 at the beginning of treatment and after 24 hours. Where present, statistical significance between the two groups at each considered time point and, for each group, between consecutive time points was reported.

5

Figure 8:
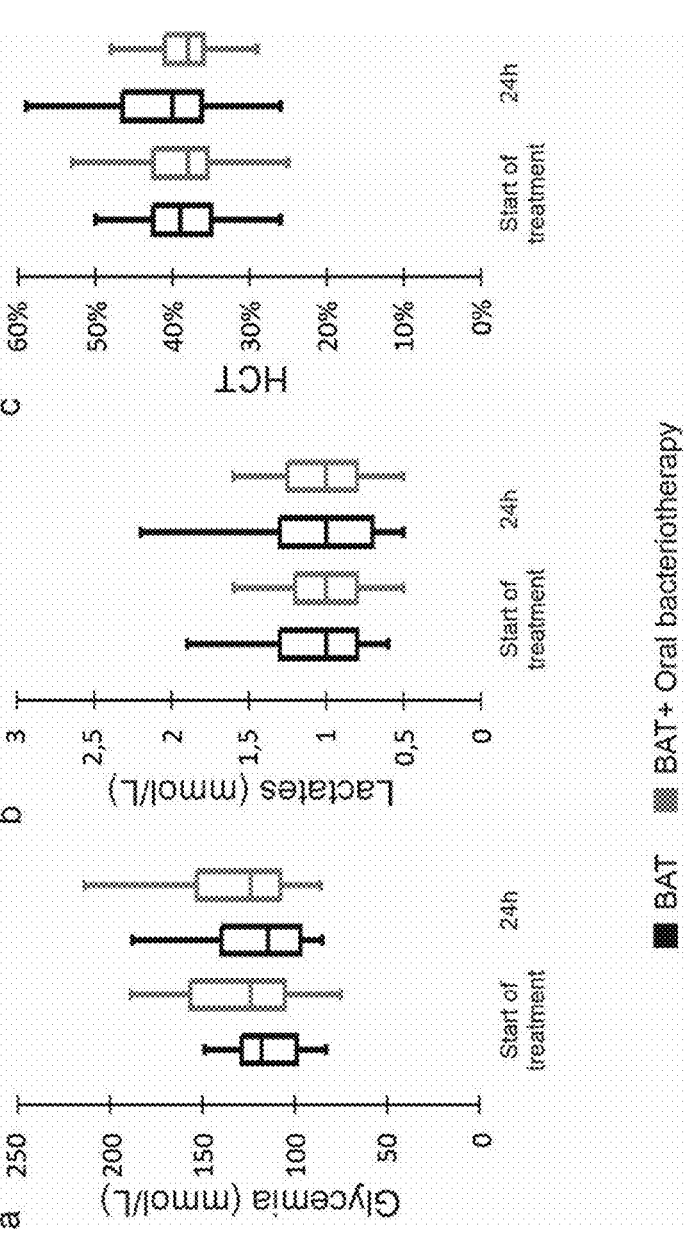

FIG. 8 shows box and whisker plots relative to the distribution of (a) blood glucose, (b) lactates, and (c) hematocrit values within the group treated with oral bacteriotherapy and the group treated with the best available therapy (BAT) for COVID-19 at the beginning of treatment and after 24 hours. Where present, statistical significance between the two groups at each considered time points and for each group between consecutive time points was reported.

Figure 9:
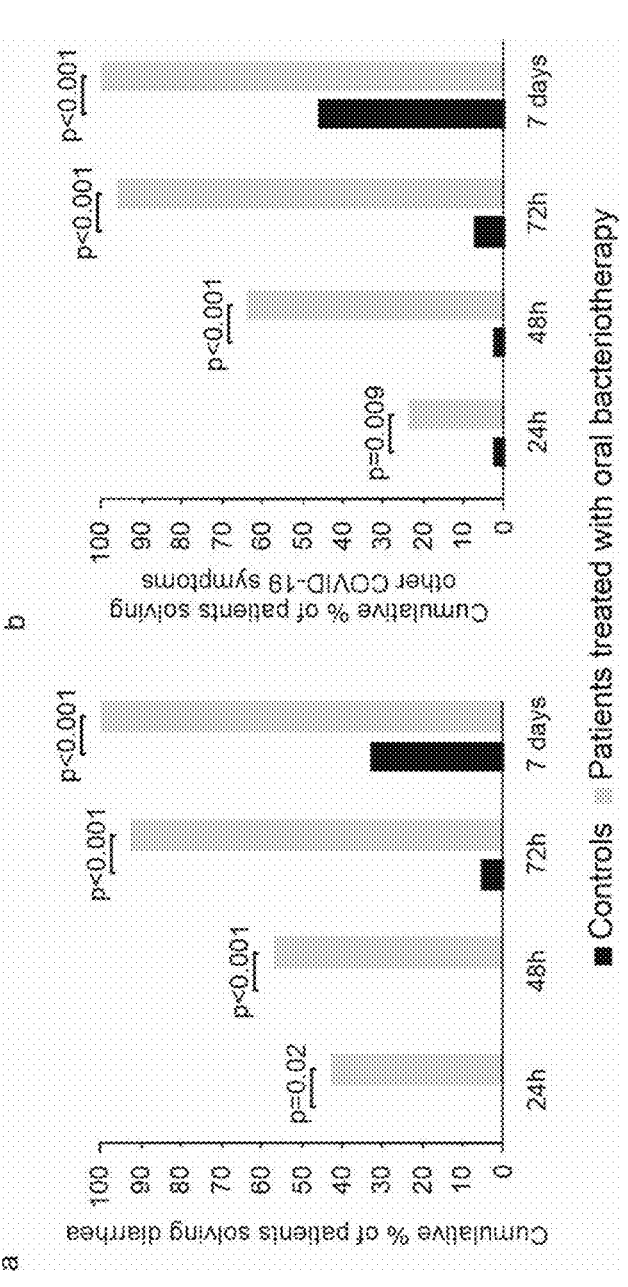

FIG. 9 show bar graphs regarding the disappearance of diarrhea (a) as well as other symptoms (b) at different successive time intervals in subjects treated with the bacteria of the invention and in untreated control subjects. The presence of statistically significant differences between the two groups of studied subjects was reported for each time interval. A $p \leq 0.05$ was considered statistically significant.

Figure 10:
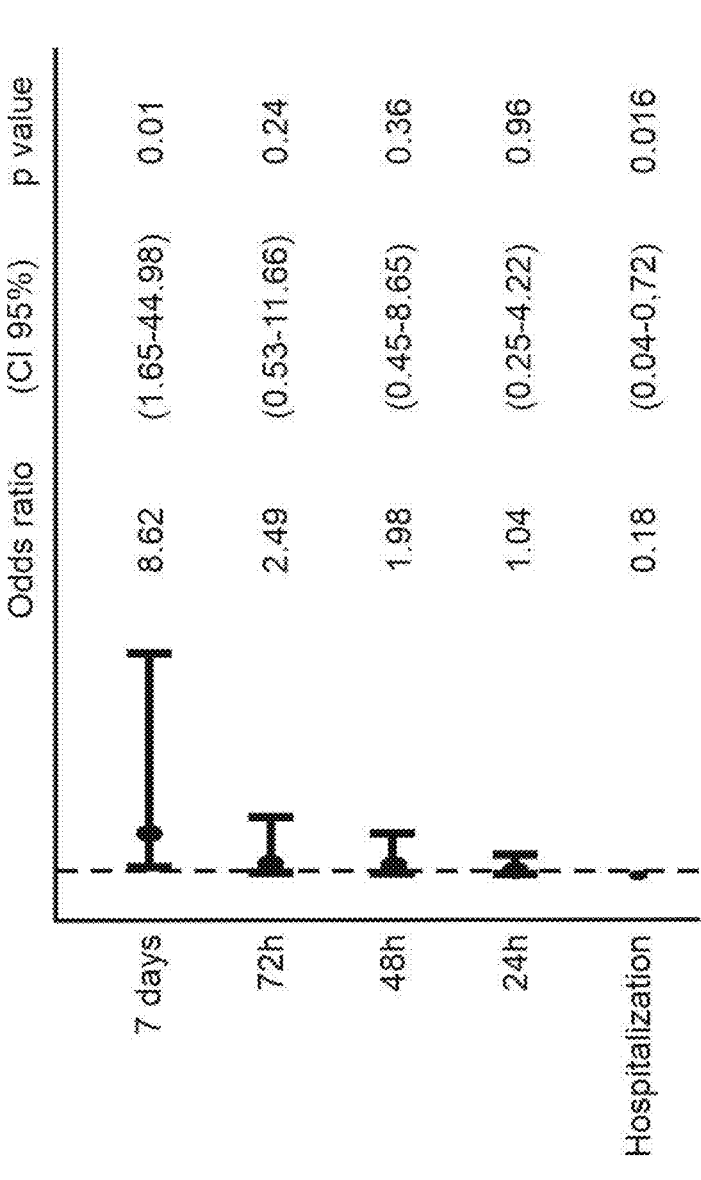

FIG. 10 shows a longitudinal analysis of data on the occurrence of respiratory failure in relation to the control vs. treated group performed by the linear generalized mixed model (GLIMMIX™, SAS Institute Inc., Cary, NC, USA). The odds ratio (OR) the relative 95% confidence interval (95% CI) and the statistical significance (p) were reported for each time point. A $p \leq 0.05$ was considered statistically significant.

Figure 11:
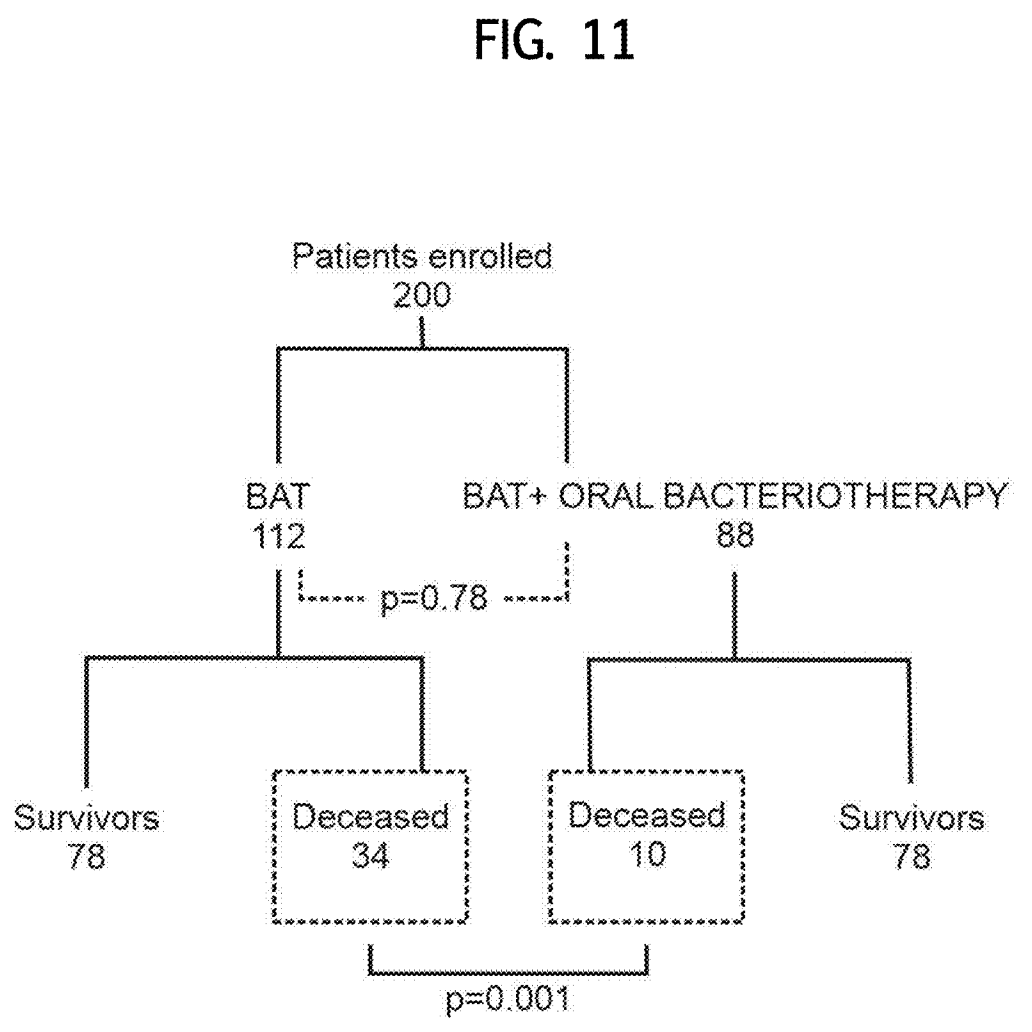

FIG. 11 shows the mortality in ICU wards in the two groups (BAT vs. BAT treatment plus oral bacteriotherapy, where BAT means "best available therapy".

Figure 12:
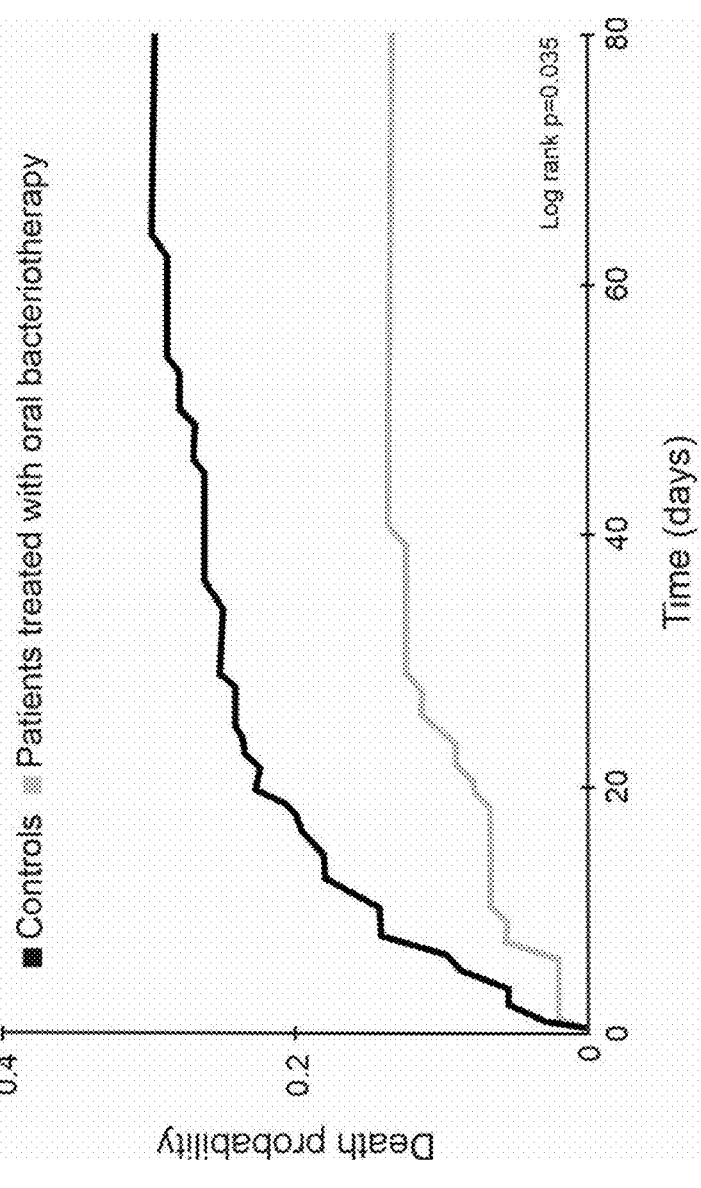

FIG. 12 presents the probabilities of death by Kaplan-Meier curves showing BAT treatment versus BAT plus oral bacteriotherapy, where BAT means "best available therapy."

Figure 13:
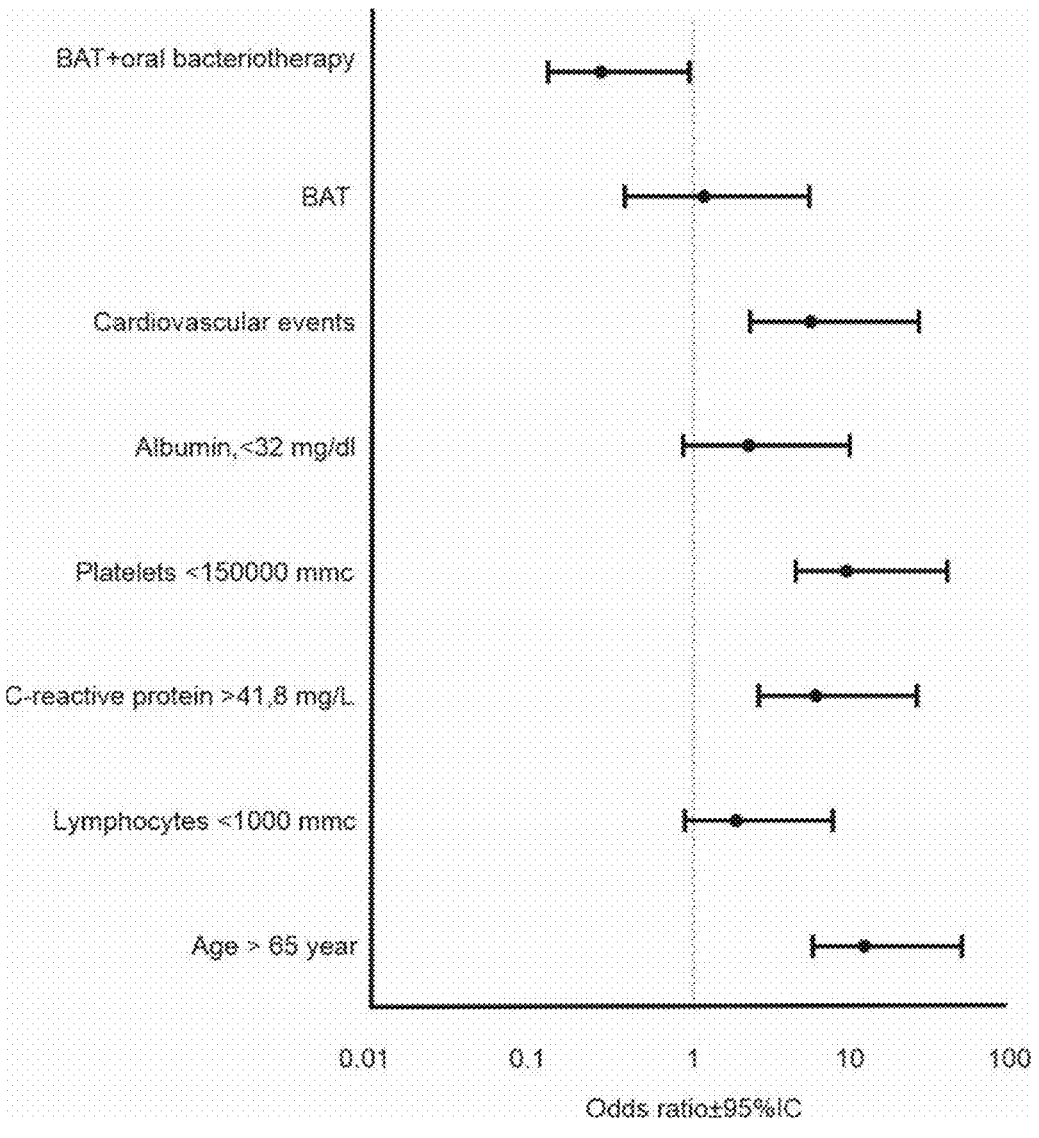

FIG. 13 shows a multivariate forest plot analysis with 95% confidence intervals.

DETAILED DESCRIPTION OF THE INVENTION

Experimental Part

Studies of coronavirus disease have been performed in humans.

Human Studies—Introduction

Understanding the invasive process of SARS-COV-2 is essential in contrasting the disease. Virus entry points into the body, such as ACE2 receptors, are known to be enzymes also expressed by intestinal cells. Coronaviruses constantly change their binding patterns along their evolution, also varying their potential target in the lungs. In contrast, this target tends to remain constant at the level of the intestine. Gut mucosal cells (enterocytes) could therefore be a reservoir for coronaviruses (Feng, Z. et al., 2020). COVID-19 affects both lungs. The alveoli of the lungs fill with fluid, reducing their ability to absorb oxygen and causing shortness of breath, coughing, and other symptoms. In some individuals, respiratory problems can become so severe that they require supplemental oxygen delivery or even external ventilation assistance. In such cases, the method used by medical personnel to increase the partial pressure of oxygen ($pO_2$) in the blood is oxygen therapy, which often requires invasive medical practices.

The severity of hypoxemia (lack of blood-borne oxygen) was strongly correlated with high levels of immune cells, as well as, with markers of inflammation. The vicious cycle between hyperinflammation and gut dysbiosis appears to be associated with an elevated risk of respiratory distress with organ damage and fatal course. In the acute phase, viral DNA, has been detected in blood only in 10% of patients, while it is possible to identify it in the faeces of 50% of the analyzed subjects. The involvement of the intestine could also explain the wide variation in viral load determined by different tests performed on the same person, permitting to imagine the intestinal environment as a reservoir in which the virus can hide and remain.

It was surprisingly found that the administration of specific mixtures of bacteria are able, in a very short period of time, to significantly increase the oxygenation levels of patients with severe SARS-CoV-2 infections compared to subjects treated with conventional drug therapy alone. These mixtures also reduce the rate of disease progression and mortality. Of note, improvement in hypoxemia has never been previously described, even for other diseases affecting humans. The rapid improvement of oxygen levels in subjects treated with oral bacteriotherapy, has a number of undoubted advantages, first among which the contrast of the complications typical of acute respiratory distress syndrome (ARDS) associated with COVID-19. In addition, the greater quantity of oxygen available, in a short time, to organs and body tissues would allow to postpone the deleterious/injurious effects associated with acute hypoxia, so extending the time window in which the patient affected by COVID-19 can be effectively treated with pharmacological therapy and benefit from the antiviral and protective action of the formulations object of the present invention. The bacterial strains present in the formulations of the present invention are rich in sphingomyelinases (SMases) which lead to the production of ceramides by hydrolyzing sphingomyelin (Leyer, G J. et al., 2009; Lew, L C. and Liong, M T., 2013). Ceramides, through a series of signaling cascades, play crucial roles in distinct physiological processes, including cell membrane remodelling, migration, proliferation, differentiation, and cell death. Several studies highlight that ceramides are able to inhibit the replication of different viruses, including those responsible for influenza (Tian, Y. et al., 2019), suggesting that manipulating the metabolism of such biological macromolecules may effectively represent a therapeutic approach to counteract viral infections (Dai, L. et al., 2015, Finnegan, C M. et al., 2004; Darwiche, N. et al., 2005; Pritzl, C J. et al., 2015).

Due to this dual mechanism of action, the specific bacterial formulations claimed herein constitute a therapeutic option for the treatment of SARS-CoV-2 infections.

The estimated surface area of the gastrointestinal tract is approximately 250-400 m$^2$. This body district is the site of "physiological inflammation" produced by the endoluminal content, which exerts a protective action against many pathogenic germs. The balance that controls the "physiological inflammation" is interrupted by dysbiotic phenomena as well as by the presence of acute infections. Under normal conditions, the intestinal mucosa receives between 10% and 35% of the total cardiac output. The arteries supplying the intestine are susceptible to vasoconstriction or vasodilatation. These processes regulate blood flow to the viscera, allowing, when necessary, their increased blood supply, as happens during digestive processes. Conversely, in the presence of hypoxic conditions, the processes of vasoconstriction and vasodilation reduce the blood supply to the intestines, making oxygen more available to priority organs for survival such as the heart and brain.

Figure 1:
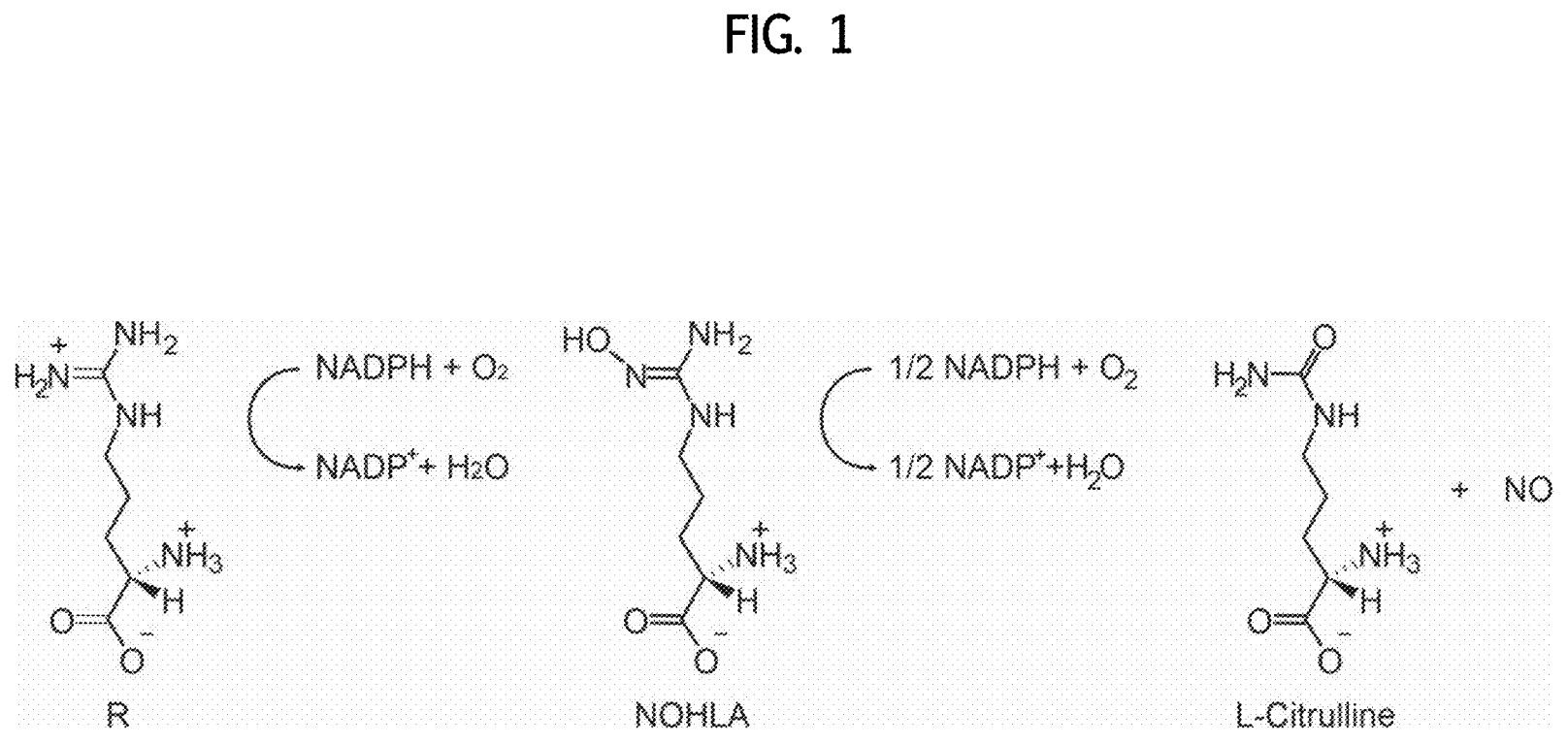
Figure 2:
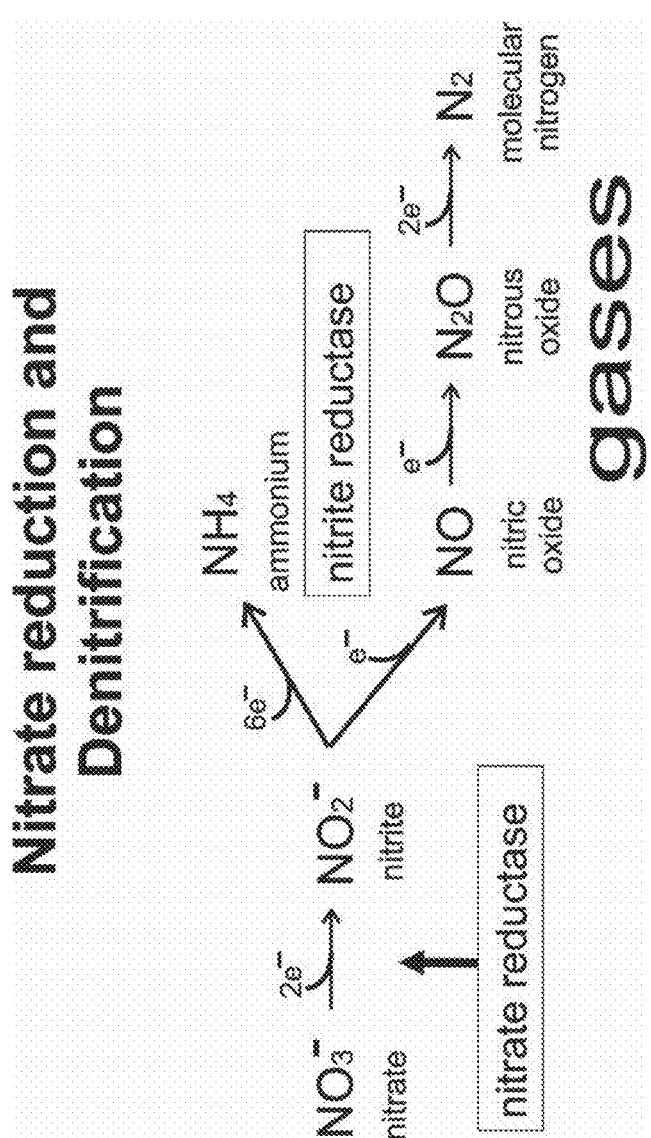
FIG. 2 shows the way through which some commensal intestinal bacteria produce nitrate and nitrite reductase, thereby producing NO.

Metabolic regulation of mucosal vasodilation is usually attributed to nitric oxide (NO). NO is a gas signaling molecule with autocrine and paracrine activity. It acts by diffusion into vascular smooth muscle and induces vasodilation. NO is generated by the activity of enzymes termed nitric oxide synthases (NOS), which are classified as constitutive NOS, dependent on calcium and calmodulin, and inducible NOS (iNOS also termed NOS2), expressed by macrophages and other cells upon pro-inflammatory cytokine activation. NOS enzymes use L-arginine and oxygen as substrates to catalyze NO formation, as shown in FIG. 1. The reaction consumes 1.5 moles of NADPH and 2 moles of oxygen. Intraluminal bacteria can also contribute to NO production near the intestinal epithelium via the inorganic nitrate reduction pathway, as shown by FIG. 2.

Whenever arterial oxygen concentration is reduced, an increase in blood flow (hypoxic vasodilation) occurs to restore oxygen delivery. COVID-19-associated hypoxic vasodilation is an adaptive response involving increases in local NO concentrations in response to an acute reduction in arterial partial pressure of oxygen caused by the extensive lung injury. Different mechanisms are implicated in this phenomenon, including increased synthesis of NO by NOS, increased reduction of $NO_2$ to NO by heme- or pterin-based enzymes, increased release of NO from storage forms of the latter, and reduced deactivation by mitochondrial cytochrome C oxidase (CcO).

Figure 3:
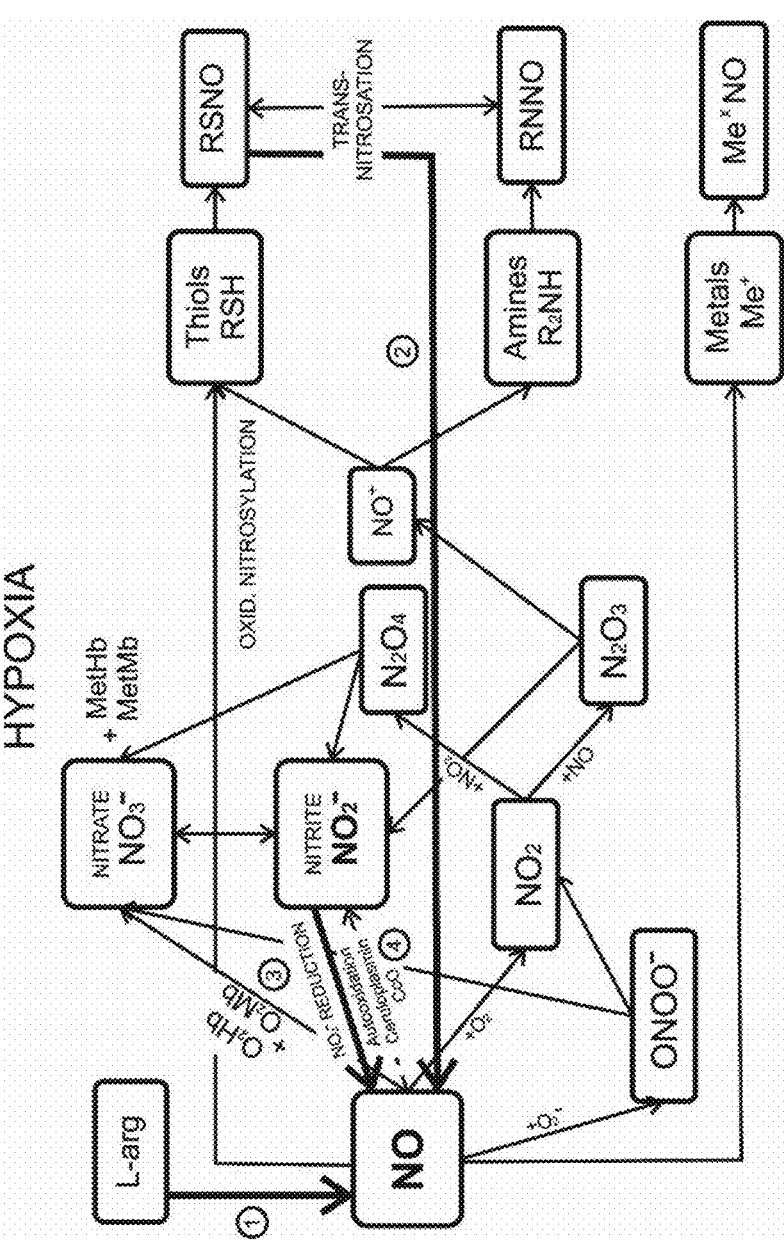
FIG. 3 shows possible mechanisms of increased NO levels under hypoxic conditions.

FIG. 3 shows possible mechanisms of increased NO levels under hypoxic conditions that include [1] increased production from NOS, [2] increased NO release from storage forms such as RSNO, [3] increased reduction from NO2, and [4] decreased metabolism from CcO.

Figure 4:
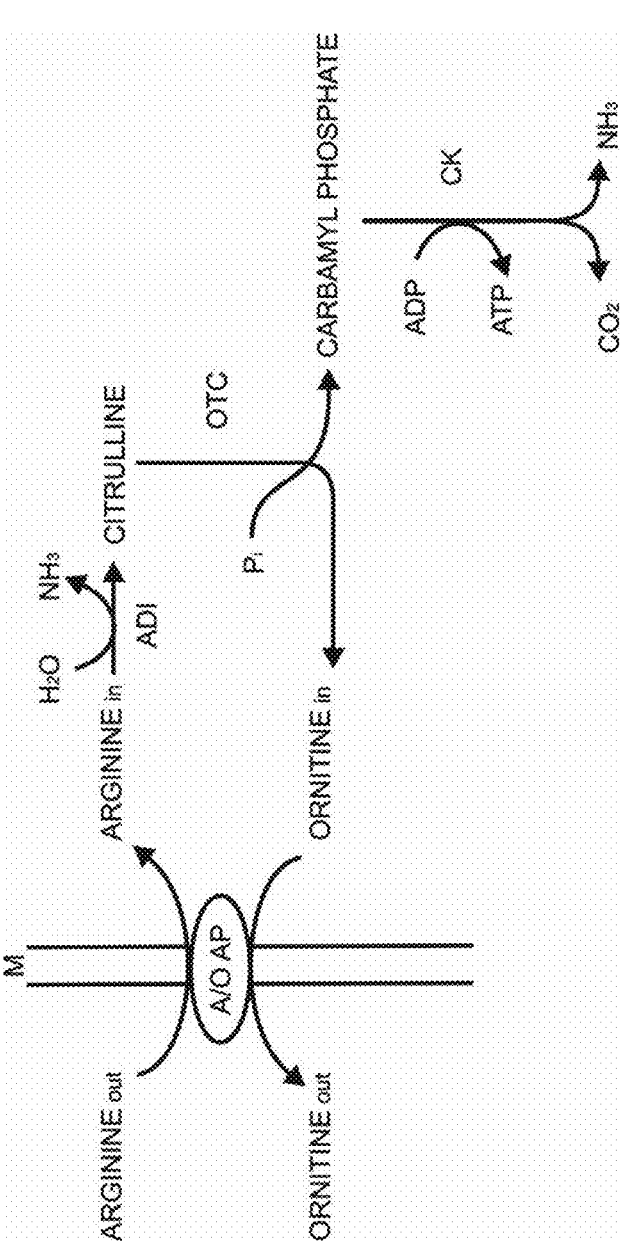
FIG. 4 shows the L-arginine deiminase pathway.

The mixtures of the present invention have the ability to inhibit NOS2 enzyme activity in in vitro models by producing the enzyme L-arginine deiminase (ADI). L-arginine deiminase (ADI) is a widely distributed enzyme within the lactic acid bacteria group (Cunin, R. et al., 1986). Organisms employing this pathway convert L-arginine to L-citrulline and ammonia. FIG. 4 shows the biosynthetic pathway catalyzed by the enzyme L-Arginine deiminase.

This enzyme, due to its higher binding affinity for L-arginine, is able to reduce the amount of this amino acid available to NOS2 synthesized by intestinal epithelial cells, thus reducing the amount of NO produced by them.

This evidence makes it possible to hypothesize an intervention of the bacterial strains contained in SIVOMIXX® (*Streptococcus thermophilus* DSM 32245, *Bifidobacterium animalis* subsp. *lactis* DSM 32246, *Bifidobacterium animalis* subsp. *lactis* DSM 32247, *Lactobacillus acidophilus* DSM 32241, *Lactobacillus helveticus* DSM 32242, *Lactobacillus paracasei* DSM 32243, *Lactobacillus plantarum* DSM 32244, and *Lactobacillus brevis* DSM 27961) on the production of NO in the intestinal lumen.

Results obtained from studies carried out on patients with severe COVID-19 treated with conventional drug therapy alone or additionally supplemented with SIVOMIXX®, have unexpectedly shown that the latter experienced a significant improvement in blood oxygenation levels as soon as 4-6 hours after the first administration of the probiotic. This improvement in blood oxygenation parameters is surprising, especially considering the degree of pulmonary impairment shown by patients at the beginning of treatment, as well as, the high improbability of a relevant restoration of the lungs' effectiveness in bringing oxygen into the bloodstream from the atmosphere in such a short period of time. In this context, the observed improvement in oxygenation parameters present as early as a few hours after the first ingestion of bacterial strains covered by the present invention suggests a metabolic mechanism of action associated with probiotic administration. FIG. 5 shows the change in oxygenation parameters at 6 h after the first treatment with such bacterial strains for a representative group of patients. Of note, inhibition of NO production to improve the prognosis of such patients is in stark contrast to what published in a very recent article that reiterates the utility of treating Covid-19 subjects with NO (Adusumilli, NC. et al., 2020).

First Human Study

In severe cases, COVID-19 affects both lungs, infecting ACE2-expressing alveolar type II cells and possibly type I cells. Along with the damage to type I and type II cells, extensive endothelial damage occurs with subsequent permeation of plasma proteins, formation of hyaline membranes and inflammatory exudate, all of which impair alveolar function. As the virus multiplies and spreads rapidly, it becomes increasingly difficult for the body to absorb oxygen. In the event that the lungs are unable, on their own, to provide the necessary oxygen supply required by the body, treatment options such as high flow nasal cannula (HFNC), non-invasive positive pressure ventilation (NIPPV), intubation and invasive mechanical ventilation, or extracorporeal membrane ventilation (ECMO) are typically applied. The goal of these therapeutic strategies was to provide external support for breathing in order to ensure adequate oxygen to the organs while waiting for lung function to be restored.

The total membrane surface area of alveoli is approximately 100 $m^2$ and represents a very efficient gas exchange interface. However, in accordance with both the physical laws governing surface tension and the La Place's law, during acute respiratory syndrome (ARDS) and pneumonia, alveoli tend to flood completely with exudate, losing their functionality, or not to flood at all, maintaining their action unchanged. However useful it may be, the treatment with oxygen does not allow to restore the functionality of a significant number of non-functioning alveoli. It should also be considered that the amount of oxygen that can be administered to an individual can not exceed a maximum threshold because of the toxicity of this gas and the pressure exerted on the alveoli. This, together with the impossibility to increase the respiratory surface and to restore the damaged areas in a short time, poses a serious problem to the oxygenation of organs and tissues of patients.

Organs need adequate amounts of oxygen to function efficiently, and if patients are infected with COVID-19 or have severe respiratory compromise for various reasons, the only solution is mechanical ventilation with all the risks that this entails.

Since the administered probiotic product has a relevant ability to inhibit the activity of the enzyme nitric oxide synthase 2 (NOS2) due to the presence in the formulation of bacteria producing L-arginine deiminase (ADI), an influence of the formulations object of the present invention on the production of nitric oxide (NO) in the intestinal lumen has been demonstrated. The decreased NO production would lead to a reduction in the oxygen consumption that such production requires and to an increased bioavailability of oxygen itself in the circulatory system. This is even more important considering that the estimated surface area of the gastrointestinal tract is approximately 250-400 $m^2$ and that, under normal conditions, the intestinal mucosa receives between 10% and 35% of the total cardiac output. Because the arteries supplying the intestine are susceptible to NO-mediated vaso-constriction or vasodilation, the local inhibition of such vasodilation together with the oxygen sparing impacts the peripheral blood level by reducing hypoxemia. Patients Enrolled patients (69; mean age 63.2±16.3 years) were positive for COVID-19. The diagnosis of COVID-19 was made by means of oropharyngeal and nasopharyngeal swabs performed in duplicate for the detection of SARS-CoV2 E and S genes by molecular method based on polymerase chain reaction. All investigated patients had the following characteristics: fever >37.5° C., need for noninvasive oxygen therapy, and involvement of more than 50% of the lung as determined by CT scan. None of the enrolled patients presented the need for intensive care unit care on admission.

Before the beginning of the treatment, and at the end of the following 24 hours, each of the enrolled subjects was subjected to blood sampling useful to carry out blood gas analysis with standard methods. The parameters considered for the study were: partial pressure of oxygen (pO$_2$), fraction of inspired oxygen (FiO$_2$), oxygenated hemoglobin (O$_2$Hb), reduced hemoglobin (HHb), lactates, blood glucose, hematocrit (HCT). Patients were considered positive for respiratory failure when the ratio of the arterial partial pressure to the fraction of inspired oxygen PaO$_2$/FiO$_2$ determined for them was <300 in accordance with the guidelines for the management of severe sepsis and septic shock, 2012 (Dellinger et al., 2012).

CT Scan

High-resolution CT scan was used to identify pulmonary involvement according to the official diagnosis and treatment protocol (6th edition) defined by the National Health Commission of China. Typical CT findings for COVID-19 are considered to be 1) ground-glass opacity, 2) consolidation, 3) reticular pattern, and 4) "crazy paving" pattern (Ye, Z. et al., 2020).

Oral Bacteriotherapy

The formulation administered in this study contains the following bacteria: *Streptococcus thermophilus* DSM32245, *Lactobacillus acidophilus* DSM32241, *Lactobacillus helveticus* DSM32242, *Lactobacillus paracasei* DSM32243, *Lactobacillus plantarum* DSM32244, *Lactobacillus brevis* DSM27961, *Bifidobacterium animalis* subsp. *lactis* DSM32246,

*Bifidobacterium animalis* subsp. *lactis* DSM32247. The levels of arginine deiminase (ADI) and sphingomyelinase (Smasi) and the ratios between the two enzymes are a key part of the formulation controls. Levels were 120 µmol L-citrulline/h/g of sphingomyelinase and 90 nmol ceramides/h/g of arginine deiminase per gram of composition, respectively. Patients were treated with a total of 10 grams of bacteria per day. Sphingomyelinase activity is valuated from bacterial extracts (from lyophilized product) by fluorometric assays that assess ceramide production through hydrolysis of C12-NBD sphingomyelin (N-{12-[(7-nitro-2-1,3-benzoxadiazole-4-yl)amino]dodecanoyl}sphingosine-1-phosphocholine) (Ala-b aster, Alabama, USA) expressed as ceramide nanomoles/h/g of initial bacterial lyophilizate. Enzymatic activity relative to arginine deiminase is determined by incubation of bacterial extracts (from lyophilized product) with L-arginine and subsequent colorimetric measurement of L-citrulline production. Enzyme activity is expressed as µmol L-citrulline/h/g of initial bacterial lyophilisate.

Statistical Methods

Sample analysis was primarily performed with tables and graphs corresponding to the type of qualitative or quantitative variables. The chi-square test was applied to the qualitative clinical variables to assess the presence of statistically significant differences between groups. The two-sided Mann-Whitney U test was used to assess the presence of statistically significant differences between groups with respect to continuous variables and Charlson index score. For each group, the presence of significant differences between successive time points was assessed by Wilcoxon signed rank tests. In all cases, a p value≤0.05 was considered statistically significant. When necessary, p values were corrected by Benjamini-Hochberg procedure in order to account for multiple comparisons.

Results

Because there are currently no codified therapies for the medical treatment of patients with COVID-19, inpatients were treated with the best available therapy (BAT) consisting of the administration of antibiotics and/or the antiviral drug Remdesivir, possibly plus oxygen, on a case-by-case basis. Data were collected and outcomes were compared between patients positive for COVID-19 who received such treatment (29; 42%) and those who were additionally treated with oral bacteriotherapy (40; 58%). The main characteristics of both groups of patients are summarized in Table 1.

TABLE 1

| | Treated group (no 40) | Control group (no 29) | p-value |
|---|---|---|---|
| Age (mean ± DS) - years | 60.4 ± 18.0 | 67.1 ± 13.0 | 0.107 |
| Gender (Male; %) | 22; 55.0% | 25; 86.2% | 0.013 |
| BMI (mean ± DS) - kg/m$^3$ | 20.6 ± 2.7 | 20.9 ± 2.2 | 0.475 |
| ALT (mean ± DS) - IU/1 | 37.1 ± 21.9 | 34.0 ± 25.3 | 0.151 |
| AST (mean ± DS) - IU/1 | 39.9 ± 64.5 | 29.4 ± 16.2 | 0.917 |
| Charlson index | 2.6 ± 2.5 | 2.9 ± 1.7 | 0.280 |
| Respiratory failure - N; %. | 18; 45.0% | 15; 51.7% | 0.758 |
| Drug therapy - No.; %. | | | |
| | | | |
| Antiviral (Remdesivir) | 8; 20.0% | 10; 34.4% | 0.283 |
| Antibiotic | 39; 97.5% | 25; 86.2% | 0.188 |
| Deaths - No.; %. | 0; 0.0% | 1; 3.4% | 0.871 |

At the beginning of the treatment, the two groups determined on the basis of the administration of SIVOMIXX® containing bacterial strains of the present invention were homogeneous with respect to all the parameters considered, except sex. No significant difference was found in the distribution of pharmacological therapies or mortality between the two groups, although the only death recorded was in the court of individuals treated with standard therapy only.

With regard to the PaO$_2$/FiO$_2$ ratio, which describes the severity of pulmonary dysfunction, no significant difference was shown between the two groups at the beginning of treatment, whereas significantly higher values of this ratio (a trend to improvement) were observed for the group taking SIVOMIXX® in the 24 after the start of treatment (FIG. 6 a).

Observation of the results obtained for the pO$_2$ variable (FIG. 6 b) shows that, at the start of treatment, no significant difference was observed between the two groups, while significantly higher values of this parameter were found after 24 hours in the group treated with SIVOMIXX® compared to that receiving BAT alone. In addition, both groups showed significant increases in pO$_2$ after 24 hours compared to the start of treatment. Although the FiO$_2$ values observed at the beginning of the study were not significantly different between the two groups, after 24 hours, the group treated with only BAT presented significantly higher levels of this parameter than the group treated with probiotics (FIG. 6 c). The same trend was shown at 6 hours for a limited number of subjects representative of the two groups in the study as shown in FIG. 5.

in The analysis of oxygenated hemoglobin (O$_2$Hb) levels produced results perfectly in line with those previously described for oxygen. In fact, while at the beginning of the treatment the two groups were homogeneous for this parameter, significantly higher levels of O$_2$Hb were found in the group treated with probiotics in the following 24 hours (FIG.

7 *a*). This difference can be explained by the significant temporal increase of $O_2Hb$ values in the group treated with SIVOMIXX® compared to the beginning of the treatment, while the subjects treated with BAT alone did not show significant changes in this parameter. The $sO_2$ represents the percentage of hemoglobin in arterial blood that is able to bind oxygen and is saturated with this gas. This parameter is obtained according to the formula:

$$sO_2=O_2Hb/O_2Hb+\text{reduced hemoglobin[HHb]}$$

In line with what was shown for oxygenated hemoglobin, at the beginning of treatment, $sO_2$ did not differ significantly between the two groups. At the t 24 hours after the start of treatment, significantly higher levels of $SO_2$ were observed for the group treated with SIVOMIXX® than for the group receiving BAT alone, although both groups showed significant temporal increases in this variable (FIG. 7 *b*).

No significant differences between the groups were shown for the variables blood glucose, lactates, and hematocrit both at the beginning of treatment and at the following 24 hours (FIG. 8*a*, *b*, and *c*).

Conclusions

The study shows that, in the group of subjects treated with the product SIVOMIXX® containing bacterial strains of the present invention, a significant increase in the levels of blood oxygenation was surprisingly recorded, which is evident already after 24 hours from the first intake of the product. However, this unexpected increase in oxygenation is not associated with an increase in the fraction of oxygen inhaled, nor can it be ascribed to a significant restoration of lung function, which is highly unlikely in a short time such as those considered in the study. In light of the evidence and considerations reported, it is licit to assume that the increased oxygenation of the bloodstream observed in subjects treated with SIVOMIXX® comes from alternative sources than those arising from the exchange of gas in the lungs and is associated with the administration of the probiotic mixture. In this context, it is plausible that at least part of the increased blood oxygenation is due to the action of arginine deiminase (ADI) produced by the bacterial strains contained in SIVOMIXX®. This enzyme, by competitively inhibiting enzymes responsible for the formation of nitric oxide, is able to modulate the production of this molecule by keeping available oxygen reserves that would inevitably be used in the biosynthetic pathway of NO.

Observational Study

The study aims to evaluate the improvement of symptomatology as well as the risk of developing respiratory failure in a representative group of hospitalized patients with a positive diagnosis of COVID-19 treated with the probiotic mixture SIVOMIXX® in addition to conventional drug therapy [hydroxychloroquine (HCQ), antibiotics (ABX) and/or tocilizumab (TCZ)]. COVID-19-positive subjects (No. 42) admitted to the same hospital ward during the same period, i.e., from Mar. 14, 2020 to Apr. 4, 2020, constituted the control group treated with conventional therapy alone. The results obtained provide evidence of the importance of the gut-lung axis in COVID-19 infection, the modulation of which induces a rapid and significant improvement in the clinical picture, as well as a significant reduction in the risk of developing pulmonary insufficiency and/or incurring fatal events (no deaths recorded in the group treated with probiotics compared to four deaths in the control group). With all necessary precautions, the data show that an effective therapeutic action at the intestinal level induces a beneficial reaction at the pulmonary level.

The study aims to evaluate the improvement of symptomatology as well as the risk of developing respiratory failure in a representative group of hospitalized patients with a positive diagnosis of COVID-19 treated with the probiotic mixture SIVOMIXX® in addition to conventional drug therapy [hydroxychloroquine (HCQ), antibiotics (ABX) and/or tocilizumab (TCZ)]. COVID-19-positive subjects (No. 42) admitted to the same hospital ward during the same period, i.e., from Mar. 14, 2020 to Apr. 4, 2020, constituted the control group treated with conventional therapy alone. The results obtained provide evidence of the importance of the gut-lung axis in COVID-19 infection, the modulation of which induces a rapid and significant improvement in the clinical picture, as well as a significant reduction in the risk of developing pulmonary insufficiency and/or incurring fatal events (no deaths recorded in the group treated with probiotics compared to four deaths in the control group). With all necessary precautions, the data show that an effective therapeutic action at the intestinal level induces a beneficial reaction at the pulmonary level.

Patients

A total of 70 patients with a positive diagnosis of COVID-19 (mean age 59.9±14.2 years) were enrolled in the present study. Diagnosis of COVID-19 was performed by oropharyngeal and nasopharyngeal swabs performed in duplicate for detection of SARS-CoV2 E and S genes by polymerase chain reaction-based molecular method. Patients presented with dyspnea (44, 62.9%), fever (66, 94.3%), cough (54, 77.1%), fatigue (15, 21.4%), myalgias (4, 5.7%), diarrhea (33, 47.1%), while 56 (80.0%) were characterized by the presence of comorbidities in a range of 1 to 6.

Dyspnea was defined as "a subjective experience of respiratory disickness consisting of qualitatively distinct sensations of varying intensity" (Laviolette, L. et al., 2014). Patients were considered positive for respiratory failure when the $PaO_2/FiO_2$ ratio, determined for them, was less than 300 in accordance with the guidelines for the management of severe sepsis and septic shock, 2012 (Dellinger et al., 2012). Acute diarrhea was defined as stools with increased water content, volume, or frequency, lasting less than 14 days (Barr, W. and Smith, A., 2014).

All patients studied did not present with a need for ICU assistance at the time of admission.

For each patient, body mass index (BMI), Charlson comorbidity index, oxygen support requirement, and laboratory values including alanine aminotransferase (ALT), aspartate aminotransferase (ALT), hemoglobin (Hb), pH, hydrogen carbonate ($HCO_3$), lactic acid, and arterial carbon dioxide pressure ($PaCO_2$) were determined at the start of treatment. Observed arterial oxygen partial pressure ($PaO_2$), fraction of inspired oxygen $FiO_2$, disappearance of COVID-19-associated symptoms, adverse events, and number of patients transferred to the ICU were collected at 24 hours, 48 hours, 72 hours, and 7 days after the start of oral bacteriotherapy and hospitalization for all patients independently of the treatment used. Patients were considered positive for respiratory failure when the $PaO_2/FiO2$ ratio determined was <300. Because this was a retrospective collection of real-life emergency data, some laboratory data were not available. In particular, when there was significant improvement in clinical and respiratory gas exchange, sometimes the physician did not repeat the follow-up blood gas analysis, considering it an unnecessary invasive pain procedure.

CT SCAN

High-resolution CT scan was used to identify pulmonary involvement according to the official diagnosis and treatment protocol (6th edition) defined by the National Health Commission of China. Typical CT findings for COVID-19 are considered to be 1) ground-glass opacity, 2) consolidation, 3) reticular pattern, and 4) "crazy paving" pattern (Ye, Z. et al., 2020).

Oral Bacteriotherapy

The formulation administered in this study contains the following bacteria: *Streptococcus thermophilus* DSM32245, *Lactobacillus acidophilus* DSM32241, *Lactobacillus helveticus* DSM32242, *Lactobacillus paracasei* DSM32243, *Lactobacillus plantarum* DSM32244, *Lactobacillus brevis* DSM27961, *Bifidobacterium animalis* subsp. *lactis* DSM32246, *Bifidobacterium animalis* subsp. *lactis* DSM32247. The levels of arginine deaminase (ADI) and sphingomyelinase (Smase) and the ratios between the two enzymes are a key part of the formulation controls. Levels were 120 nmol L-citrulline/h/g of sphingomyelinase and 90 nmol ceramides/h/g of arginine deaminase per gram of composition, respectively. Patients were treated with a total of 2.4 billion bacteria per day. divided into three equal doses. Sphingomyelinase activity is assessed from bacterial extracts (from lyophilized product) by fluorometric assays that can evaluate ceramide production following hydrolysis of C12-NBD sphingomyelin (N-{12-[(7-nitro-2-1,3-benzoxadiazole-4-yl)amino]do-decanoyl}sphingosine-1-phosphocholine) (Alabaster, Ala., USA) expressed as ceramide nanomoles/h/g of initial bacterial lyophilizate. Enzyme activity relative to arginine deaminase is determined by incubation of bacterial extracts (from lyophilized product) with L-arginine and subsequent colorimetric measurement of L-citrulline production. Enzyme activity is expressed as μmol L-citrulline/h/g of initial bacterial lyophilized product.

Statistical Methods

Sample analysis was primarily performed with tables and graphs corresponding to the type of qualitative or quantitative variables. The chi-square test was applied to qualitative clinical variables to assess the presence of statistically significant differences between groups. The Mann-Whitney U two-sided test was used for continuous variables and Charlson index score.

Longitudinal data analysis for the variable onset of respiratory failure in relation to the control vs. treated comparison was performed using the generalized linear mixed model (GLIMMIX) considering the binary model as the distribution and logit as the connecting function (The GLIMMIX procedure. SAS/STAT User's Guide. 2009, Version 9.2). All statistical analyses were performed using SAS v. 9.4 (SAS Institute Inc., Cary, NC, USA). A p value ≤0.05 was considered statistically significant.

Results

Because there are currently no codified therapies or guidelines for the medical treatment of COVID-19 patients, hospitalized patients were treated with hydroxychloroquine, antibiotics, and/or tocilizumab, possibly plus oxygen, on a case-by-case basis. The data collected were used to compare patients with COVID-19 who received such treatment with those additionally supplemented with oral bacteriotherapy.

The two groups of patients determined on the basis of oral bacteriotherapy administration were homogeneous with respect to characteristics such as age, sex, BMI, ALS, AST, Hb, Charlson co-morbidity index, and prevalence of COVID-19-associated symptoms such as diarrhea, fever, cough, dyspnea, asthenia, and myalgia. Table 2 provides the characteristics of the patient groups obtained according to the administration of bacterial therapy. The p values are relative to the chi-square test and the Man-Whitney U test performed on discrete and continuous clinical variables, respectively. A p value ≤0.05 was considered statistically significant.

TABLE 2

|  | Treated group | Control group | p-value |
|---|---|---|---|
| Age (mean ± SD) - years | 59.0 ± 14.4 | 60.5.7 ± 14.2 | 0.764 |
| Sex (Male; %) | 17; 60.7% | 24; 57.1% | 0.766 |
| BMI (mean ± SD) - kg/m³ | 24.7 ± 3.5 | 23.4 ± 3.5 | 0.084 |
| ALT (mean ± SD) - IU/l | 22.7 ± 10.5 | 30.5 ± 22.2 | 0.337 |
| AST (mean ± SD) - IU/l | 37.0 ± 33.5 | 40.5 ± 33.0 | 0.749 |
| Hb (mean ± SD) - g/dl | 12.6 ± 1.5 | 12.8 ± 2.0 | 0.578 |
| Charlson index (mean ± SD) | 1.9 ± 1.6 | 2.3 ± 2.3 | 0.817 |
| Symptoms |  |  |  |
| Fever (No.; %) | 27; 96.4% | 39; 92.9% | 0.528 |
| Cough (No.; %) | 22; 78.6% | 32; 76.2% | 0.816 |
| Dyspnea (No.; %) | 20; 71.4% | 24; 57.1% | 0.226 |
| Asthenia (No.; %) | 6; 21.4% | 9; 21.4% | 1.0 |
| Headaches (No.; %) | 3; 10.7% | 8; 19.0% | 0.348 |
| Myalgia (No.; %) | 2; 7.1% | 2; 4.8% | 0.674 |
| Diarrhea (No.; %) | 14; 50.0% | 19; 45.2% | 0.696 |

Although there was variability in the drugs administered, the groups did not differ significantly with respect to the number, type, and combinations of drugs used during the observation period. Table 3 shows the therapies administered to the two groups of patients. The p values are for nonparametric tests, as reported in Statistical Methods. A p value ≤0.05 was considered statistically significant.

TABLE 3

|  | Treated group | Control group | p-value |
|---|---|---|---|
| Drug therapy - No.; %. |  |  |  |
| HCQ | 25; 89.3% | 40; 95.2% | 0.343 |
| TCZ | 7; 25.0% | 16; 38% | 0.253 |
| ABX | 11; 39.3% | 21; 50.0% | 0.378 |
| Number of drugs - No.; %. |  |  |  |
| 0 | 2; 7.1% | 1; 2.4% |  |
| 1 | 13; 46.4% | 11; 26.2% | 0.163 |
| 2 | 9; 32.1% | 24; 57.1% |  |
| 3 | 4; 14.3% | 6; 14.3% |  |
| Drug combinations - No.; %. |  |  |  |
| HCQ/TCZ/ABX | 4; 14.3% | 6; 14.3% | 1 |
| HCQ/TCZ | 2; 7.1% | 9; 21.4% | 0.108 |
| HCQ/ABX | 6; 21.4% | 15; 35.7% | 0.201 |
| TCZ/ABX | 1; 3.6% | 0; 0.0% | 0.217 |

Table 4 shows the respiratory parameters presented by the two groups of subjects at the beginning of the study. The results of the statistical analysis show that no significant difference was present between the two groups with respect to $PaO_2/FIO_2$, describing the severity of pulmonary parenchymal dysfunction. No significant difference between the two groups was also observed for the other parameters considered including the prevalence of subjects requiring ventilation support.

TABLE 4

| | Treated group | Control group | p-value |
|---|---|---|---|
| $PaO_2/FiO_2$ (mean ± SD) - mmHg | 316.7 ± 123.0 | 349.4 ± 99.2 | 0.21 |
| $FiO_2$ (mean ± SD) | 34.0 ± 13.0 | 49.5 ± 68.9 | 0.72 |
| $SO_2$ (mean ± SD) | 97.9 ± 2.2 | 98.1 ± 1.8 | 0.89 |
| ph (mean ± SD) | 7.5 ± 0.1 | 7.5 ± 0.0 | 0.71 |
| $HCO_3$ (mean ± SD) - mmol/L | 25.5 ± 3.4 | 25.6 ± 2.7 | 0.96 |
| Lactates (mean ± SD) - mmol/L | 1.0 ± 0.4 | 0.9 ± 0.3 | 0.56 |
| $pO_2$ (mean ± SD) - mmol/L | 92.9 ± 27.8 | 90.7 ± 28.9 | 0.62 |
| $pCO_2$ (mean ± SD) - mmol/L | 35.2 ± 6.5 | 38.3 ± 13.9 | 0.40 |
| Oxygen support - No.; %. | | | |
| Non-invasive ventilation - No.; % | 25; 89.3% | 38; 90.5% | 0.87 |
| Positive pressure ventilation - No.; % | 3; 10.7% | 3; 7.1% | 0.60 |

With regard to the resolution of symptoms associated with COVID-19, the results obtained showed that already at 24 hours from the first administration of the product SIVOM-IXX® containing bacterial strains of the present invention, the group supplemented with oral bacteriotherapy presented a significantly higher proportion of subjects with resolution of diarrhea than the group treated with conventional drug therapy, as shown in FIG. 9a. This significant difference was maintained up to 7 days with a gap between the two groups increasing as time went by. It is noteworthy that already at three days from the start of treatment, more than 90% of patients taking SIVOMIXX® had experienced the disappearance of diarrhea while, after seven days, this condition extended to all subjects in the group. Differently, after 7 days of treatment, the proportion of subjects treated with conventional pharmacological therapy that was characterized by resolution of diarrhea was lower than that shown by the group treated with probiotic at 24 hours after the start of treatment.

The other symptoms, considered cumulatively, also showed a similar trend, but with a more limited effect within 24 hours of bacterial administration (FIG. 9b).

With regard to respiratory outcome, on admission, a significantly higher percentage of patients with respiratory failure was present in the treated group than in the control group, as determined by the chi-square test (Controls 11/42, 26.2%; Treated 14/28, 50%; p value=0.042).

By applying a generalized linear mixed model, it was possible to show a significant difference in the evolution of respiratory outcome between the treated group and the control one (p=0.0002). Specifically, the calculated model showed that after seven days of treatment, patients administered with SIVOMIXX® had an 8-fold lower risk of evolving respiratory failure than individuals taking conventional therapy, as shown in Table 5 and FIG. 10.

Parameters useful in assessing the goodness-of-fit of the calculated model such as estimation statistics, covariance parameter estimates, and Type III tests for fixed effects are reported in Tables 6-8 below.

TABLE 6

| Estimation statistics | |
|---|---|
| −2 Res Log Pseudo-Likelihood | 1696.73 |
| Generalized chi-square | 195.26 |
| Generalized chi-square/DF | 0.57 |

TABLE 7

| Estimates of covariance parameters | | | |
|---|---|---|---|
| Covariance parameter | Subject | Estimate | Standard error |
| Intercept | Subject Id | 4.0087 | 1.2331 |
| AR(1) | Subject Id | 0.2394 | 0.0906 |
| Residual | | 0.5743 | 0.0711 |

TABLE 8

| Type III testing for fixed effects | | | | |
|---|---|---|---|---|
| Effect | DF Number | Den DF | F-value | Pr > F |
| Time | 4 | 272 | 5.34 | 0.0004 |
| Treatment | 1 | 272 | 0.48 | 0.4884 |
| Time*Treatment | 4 | 272 | 5.72 | 0.0002 |

Mortality and the number of patients transferred from the sub-intensive care unit to the intensive care unit are shown in Table 9 below.

TABLE 9

| | Treated group | Control group | p-value |
|---|---|---|---|
| Patients affected by inauspicious event (No.; %) | 0; 0.0% | 4; 9.5% | 0.093 |
| Patient transferred to ICU (No.; %) | 0; 0.0% | 2; 4.8% | 0.241 |

The control group had a mortality rate in line with the mortality rate reported for the Italian territory in the same period of the study (9.9%±1.7% number of deaths/total number of cases), while all 28 patients treated with oral bacteriotherapy survived at the end of the observation period.

Conclusions

The results obtained from the presented study show the association between the intake of the probiotic SIVOM-

TABLE 5

| Difference of least squares means for the combination Time*Treatment | | | | | | | | | | | |
|---|---|---|---|---|---|---|---|---|---|---|---|
| Treatment | Time | Treatment | Time | Solution | Standard error | DF | t value | PR > \|t\| | Alpha | Odds ratio | Confidence interval (95%) for odds ratio |
| NO | 0 h | YES | 0 h | −1.73 | 0.71 | 272 | −2.45 | 0 02 | 0.05 | 0.176 | 0.04-0.71 |
| NO | 24 h | YES | 24 h | 0.04 | 0.71 | 272 | 0.05 | 0.96 | 0.05 | 1.037 | 0.26-4.17 |
| NO | 48 h | YES | 48 h | 0 68 | 0.74 | 272 | 0.92 | 0 36 | 0.05 | 1.977 | 0.46-8.53 |
| NO | 72 h | YES | 72 h | 0.93 | 0.78 | 272 | 1.18 | 0.24 | 0.05 | 2.492 | 0 54-11 51 |
| NO | 7 days | YES | 7 days | 2.15 | 0.83 | 272 | 2.59 | 0.01 | 0.05 | 8 62 | 1.67-44.43 |

IXX®, containing bacteremic strains according to the present invention and the rapid resolution of symptoms commonly associated with COVID-19. Such resolution appears to be only limited in subjects not receiving the treatment in the same time frame. In addition, a protective effect of SIVOMIXX® administration against the development of respiratory failure in subjects with SARS-CoV2 infection was shown.

Retrospective Study

The following are the results of a larger "real-life" study concerning the complementary use of the bacterial composition formed by *Streptococcus thermophilus* DSM 32245, *Bifidobacterium animalis* subsp. *lactis* DSM 32246, *Bifidobacterium animalis* subsp. *lactis* DSM 32247, *Lactobacillus acidophilus* DSM 32241, *Lactobacillus helveticus* DSM 32242, *Lactobacillus paracasei* DSM 32243, *Lactobacillus plantarum* DSM 32244, and *Lactobacillus brevis* DSM 27961 (SIVOMIXX®) in a cohort of individuals infected with SARS-CoV2 and receiving best available therapy (BAT).

Materials and Methods

The one reported represents a retrospective "real-life" observational cohort study aimed at comparing patients with severe COVID-19-associated pneumonia treated with best available therapy (BAT) and patients additionally supplemented with oral bacteriotherapy with respect to crude mortality rate, need for intensive care unit (ICU) hospitalization, and duration of hospitalization. To this end, the study included subjects admitted to the wards of the Department of Infectious Diseases, Policinico Umberto I Hospital, La Sapienza University of Rome, Italy, from March 6 to Apr. 26, 2020.

Patients

The diagnosis of COVID-19 was defined by positivity to oropharyngeal and nasopharyngeal swabs performed in duplicate for the detection of SARS-CoV2 E and S genes by molecular method based on polymerase chain reaction.

The study population included subjects over the age of 18 years.

All hospitalized patients received pharmacological therapy, including administration of hydroxychloroquine (200 mg twice daily for 7 days), azithromycin (500 mg once daily for 7 days), lopinavir-ritonavir (400/100 mg twice daily) or darunavir-cobicistat (800/150 mg once daily) for 14 days, and low molecular weight heparin for deep vein thrombosis prophylaxis as recommended at the time by the Italian Society of Infectious Diseases. Tocilizumab (8 mg/kg up to a maximum of 800 mg per dose with an interval of 12 h for two times) was administered in the presence of elevated serum IL-6 levels or significant worsening of the respiratory pattern in case of unavailability of IL-6 dosage. Patients admitted to the ward presenting with intestinal symptoms were given oral bacteriotherapy in addition to BAT. The formulation was administered in three daily doses of equal magnitude, for a total of 2,400 billion bacteria per day.

Variables considered for the study included: age, sex, date of hospital admission and discharge, length of stay (LOS); cardiovascular (CV) disease, chronic lung disease, chronic kidney disease (CKD), hypertension, asthma, chronic obstructive pulmonary disease (COPD), diabetes mellitus, immunodeficiency, and cancer (defined as active or past/resolved).

For each patient, the Charlson comorbidity index was determined to assess the risk of 1-year mortality in the presence of a range of comorbid conditions.

The following parameters were used to define the severity of pneumonia: Confusion-Blood urea-Respiratory rate-Blood pressure score (CURB), Confusion-Blood urea-Respiratory rate-Blood pressure, Age 65 (CURB-65), Confusion-Blood urea-Respiratory rate-Blood pressure, Age 65, Lactate dehydrogenase, platelets and albumin (CURB-65 expanded), Pneumonia severity index (PSI) score. Comorbidity-Age-Lymphocytes-Lactate dehydrogenase (CALL) were considered to predict progression of COVID-19.

Statistical Analysis

Statistical analyses were performed using the Statistical Pro-Gram for the Social Sciences (SPSS), version 22 (IBM SPSS, Chicago, III). Continuous variables were presented as medians and the interquartile range (IQR, 25°-75°), whereas the presence of statistically significant differences between groups was assessed using the nonparametric Mann-Whitney U test. Dichotomous variables were expressed as simple frequencies and percentages (%) and then compared using the chi-square test. A multivariate stepwise regression analysis was performed with several potentially confounding factors, with age >65 years, lymphocytes <1,000 in 1 μL of blood, platelets <150-103/mm$^3$, albumin <32 g/dL, CV events, BAT therapy, and oral antibacterial therapy as the dependent variable. a standard survival analysis was done by tracing participants from clinic entry to discharge or death. The event-free survival in follow-up was depicted graphically by Kaplan-Meier's survivor curve, using multivariable Cox regression analysis, including confounders with fixed baseline covariates. The effect of treatment was shown using an unadjusted odds ratio (OR) adjusted with 95% confidence interval (95% CI). The main sources of uncertainty were identified in the parameters age, C-reactive protein (CRP), Charlson comorbidity index, CURB, CURB-65, PSI, CALL, lymphocyte count, and platelet count, which were likely causes of both treatment allocation and outcome risk. In all cases, a two-tailed p value ≤0.05 was considered statistically significant.

Results

The data used are for patients positive for SARS-CoV-2 infection admitted to the wards of the Department of Infectious Diseases during the period March 6-Apr. 26, 2020. A population of two hundred patients whose demographic and clinical characteristics are described in Table 10 below was included within the study.

TABLE 10

| Parameter | Mean ± SD | Median(IQR 25-75%) | Number(%) |
|---|---|---|---|
| Gender, Male/Female | | | 113(57)/83(43) |
| Age | 63 ± 15 | 63(54-75) | |
| Males | 62 ± 15 | | |
| Females | 64 ± 16 | | |
| White blood cells | 6261.5 ± 2766.4 | 5660(4420-7205) | |
| Neutrophils (mm$^3$) | 4606.7 ± 2641.8 | 4050(2795-6664) | |
| Neutrophils (%) | 70.8 ± 13.1 | 72.3(63.3-81) | |

TABLE 10-continued

| Parameter | Mean ± SD | Median(IQR 25-75%) | Number(%) |
|---|---|---|---|
| Lymphocytes (mm$^3$) | 1083.4 ± 649.2 | 920(670-1330) | |
| Lymphocytes (%) | 19.2 ± 10.6 | 16.8(11.5-29) | |
| Monocytes (%) | 362.2 ± 160.6 | 320(250-470) | |
| C Reactive Protein (mg/l) | 98855.8 ± 121164.2 | 53165(16937.5-140025) | |
| D-dimer(mg/l) | 1321.6 ± 1200.0 | 878(495.5-1547) | |
| Albumin(mg/l) | 36.9 ± 5.7 | 37.5(33-42) | |
| LDH(U/l) | 333.0 ± 168.5 | 288(226.5-391) | |
| Plates (mm$^3$) | 225087 ± 91489 | 208000(161250-262500) | |
| Hospital stay (days) | 20 ± 13.8 | 15(10-27) | |
| Charlson index | 2.6 ± 2.2 | 2(1-4) | |
| CURB-65 | 1.1 ± 0.8 | 1(0-2) | |
| EXP CURB-65 | 2.2 ± 1.4 | 2(0-3) | |
| PSI | 73.4 ± 29.6 | 70(51-89) | |
| CALL | 8.7 ± 2.6 | 9(7-11) | |
| Death | | | 44(22) |

Although for the sample of patients under study it was not possible to determine the duration of symptoms in the period before hospitalization, it is reasonable to assume that hospitalization occurred within a few days of the onset of respiratory symptoms because there is an efficient and free health service in the Lazio Region. The median duration of hospitalization was 15 days [IQR, (10-27)]. Of the 200 patients, 112 received BAT without oral bacteriotherapy, whereas for 88 subjects BAT was accompanied by the administration of oral bacteriotherapy. The characteristics of the two groups are shown in Table 11. Oral bacteriotherapy was started after a median value of 1 day (min 0, max 2) after hospital admission.

TABLE 11

| Parameters | BAT (n = 112) | BAT + oral bacteriotherapy (n = 98) | p-value |
|---|---|---|---|
| Gender Male/Female No. (%) | 64(57)/48(43) | 46(56)/39(44) | 0.978 |
| Median age (IQR 25-75%) | 63(55-75) | 63(52-72) | 0.289 |
| Age >65 years No. (%) | 53(47) | 38(43) | 0.448 |
| Lymphocytes <1,000 (mm$^3$) No. (%) | 60(54) | 49(56) | 0.808 |
| Platelets <150,000 (mm$^3$) No. (%) | 16(14) | 22(25) | 0.718 |
| Albumin <32 (mg/dl) No. (%) | 20(18) | 7(8) | 0.024 |
| C Reactive Protein >41.8(mg/L) N. (%) | 64(57) | 40(45) | 0.055 |
| White blood cells (mm$^3$) median (IQR 25-75%) | 5740(4570-7450) | 5.590(4.327-7155) | 0.803 |
| Neutrophils (mm$^3$) median (IQR 25-75%) | 4100(2990-5689) | 3.785(2.692-5592) | 0.528 |
| Neutrophils (%) median (IQR 25-75%) | 73(65-80) | 68(61-79) | 0.076 |
| Lymphocytes (mm$^3$) median (IQR 25-75%) | 920(640-1300) | 925(687-1.350) | 0.111 |
| Lymphocytes (%) median (IQR 25-75%) | 16(12-24) | 18(11-28) | 0.162 |
| Monocytes (mm$^3$) median (IQR 25-75%) | 320(250-450) | 325(240-470) | 0.562 |
| C Reactive Protein(mg/L) median (IQR 25-75%) | 63540(22375-160770) | 34900(12375-113970) | 0.020 |
| Median D-dimer (mg/dl) (IQR 25-75%) | 1268(627-3147) | 788(484-1770) | 0.188 |
| Median Albumin (mg/dl) (IQR 25-75%) | 37(32.0-40) | 39(34-42) | 0.008 |
| Median LDH(U/L)(IQR 25-75%) | 310(242.3-419.3) | 272(211-379) | 0.012 |
| Median Charlson index (IQR 25-75%) | 2(1-4) | 2(1-4) | 0.313 |
| CURB-65 median (IQR 25-75%) | 1(0-2) | 1(±1) | 0.395 |
| EXP CURB-65 median (IQR 25-75%) | 2(1-3) | 2(±1) | 0.108 |
| Median PSI(IQR 25-75%) | 73(54-91) | 71(±28) | 0.211 |
| Median CALL(IQR 25-75%) | 9(7-11) | 9(±3) | 0.869 |

TABLE 11-continued

| Parameters | BAT (n = 112) | BAT + oral bacteriotherapy (n = 98) | p-value |
|---|---|---|---|
| Hospital stay (days) median(IQR 25-75%) | 14(8-23) | 23(±14) | 0.012 |
| Stay in intensive care (days) No. (%) | 24(19) | 16(18) | 0.847 |
| Cardiovascular diseases No. (%) | 0(0) | 0(0) | 1.000 |
| Death No. (%) | 34(30) | 10(11) | <0.001 |
| Bloodstream infections (BSI) NO. (%) | 14(13) | 7(8) | 0.211 |
| Superinfection of the lungs No. (%) | 9(8) | 8(9) | 0.904 |
| Fungal infections No. (%) | 2(2) | 0(0) | 0.158 |

The two groups were homogeneous with respect to all clinical parameters considered, with the exception of C-reactive protein, LDH and albumin.

The primary objective of the study was to evaluate the crude in-hospital mortality in the patient within each treatment group. The crude mortality in the total subject population was 22% (44 patients). Comparison of the two groups showed that the mortality within the group supplemented with oral bacteriotherapy was significantly lower than that found for the group treated with BAT alone (Table 11, FIG. 11).

The significant reduction in the risk of death present for patients treated with both BAT and oral bacteriotherapy was further confirmed after correction for age, Charlson, CURB, CURB-65, PSI, and CALL score with an OR of 0.28 (95% CI, 0.13-0.6, p=0.001). The unweighted Kaplan-Meyer curves shown in FIG. 12 highlight the beneficial effect of the combined use of BAT and oral bacteriotherapy on the probability of death parameter.

Based on the multivariate analysis conducted, age >65 years, C-reactive protein >41.8 mg/L, platelets <150,000 mm$^3$, and cardiovascular events were associated with increased risk of mortality, whereas administration of oral bacteriotherapy was an independent variable associated with reduced risk of death (FIG. 13).

Conclusions

The retrospective court analysis clearly showed that in patients with COVID-19, characteristics such as advanced age, high levels of C-reactive protein, plateletopenia, and clinical history of cardiovascular events represent risk factors for the determination of adverse events, and that administration of one of the formulations of the present invention constitutes an independent variable associated with a significant reduction in the risk of death.

Example of Formulation 1

Lipogel Capable of Releasing Bacterial Compositions into the Oral Cavity, Nasal Cavities, Intestines for Use According to the Invention Different oily mixtures gelled through appropriate excipients and suitable delivery devices have been evaluated in order to easily administer the bacteria inside the oral cavity, nasal cavities and intestine. The main technological challenges are to ensure the biological stability of bacteria inside the lipogel even after a long period of storage and their permanence and survival in the oral cavity after application.

Composition (% by weight) of selected lipogel after pre-formulation testing:

Medium Chain Triglycerides 46%
Vitamin E acetate 50%
Microcrystalline silica 4%

Bacteria loading: in 1 gram of selected lipogel, 0.1 g of bacterial compositions can be dispersed for use according to the invention resulting in a concentration of 13.00±0.25 Log CFU/g.

Viscosity of the formulation: 400 mPa*s.

Viability: viability is maintained for up to 45 days.

BIBLIOGRAPHY

Adusumilli N C, Zhang D, Friedman J M, Friedman A J. Harnessing nitric oxide for preventing, limiting and treating the severe pulmonary consequences of COVID-19. *Nitric Oxide.* 2020 Oct. 1; 103:4-8;

Bhat, N R., Zhang, P., Bhat, A N., "Cytokine induction of inducible nitric oxide synthase in an oligodendrocyte cell line: role of p38 mitogen-activated protein kinase activation", feb 1999, J. Neurochem., 72(2):472-8;

Barr, W., Smith, A., "Acute diarrhea," 1 Feb. 2014, *Am. Fam. Physician* 89(3):180-9;

Carpinteiro A, Edwards M J, Hoffmann M, Kochs G, Gripp B, Weigang S, Adams C, Carpinteiro E, Gulbins A, Keitsch S, Sehl C, Soddemann M, Wilker B, Kamler M, Bertsch T, Lang K S, Patel S, Wilson G C, Walter S, Hengel H, Pöhlmann S, Lang P A, Kornhuber J, Becker K A, Ahmad S A, Fassbender K, Gulbins E. Pharmacological Inhibition of Acid Sphingomyelinase Prevents Uptake of SARS-CoV-2 by Epithelial Cells. Cell Rep Med. 2020 Nov. 17; 1(8):100142;

Chen L, Liu P, Gao H, Sun B, Chao D, Wang F, Zhu Y, Hedenstierna G, Wang C G. Inhalation of nitric oxide in the treatment of severe acute respiratory syndrome: a rescue trial in Beijing. Clin. Infect. Dis. 2004 Nov. 15; 39(10):1531-5;

Cunin R, Gransdorff N, Pierard A, Stalon V. Biosynthesis and metabolism of arginine in bacteria. Microbiol Rev. 1987 March; 51(1):178. Erratum for: Microbiol Rev. 50:351. PMID: 16350242; PMCID: PMC373097;

Dai, L., Trillo-Tinoco, J., Bai, A., Chen, Y., Bielawski, J., Del Valle, L., Smith, C D., Ochoa, A C., Qin, Z., Parsons, C., "Ceramide-induced apoptosis in renal tubular cells: a role of mitochondria and sphingosine-1-phoshate", 2015, *Oncotarget* 6:24246-24260;

Darwiche, N., Abou-Lteif, G., Najdi, T., Kozhaya, L., Tayoun, A A., Abou, Tayyoun, Bazarbachi, A., Dbaibo, G S., "Human T-cell lymphotropic virus type I-transformed T-cells have a partial defect in ceramide synthesis in response to N-(4-hydroxy-phenyl)retinamide", 2005, *Biochem.* J. 392:231-239;

Darwish I, Miller C, Kain K C, Liles W C. Inhaled nitric oxide therapy fails to improve outcome in experimental severe influenza. *Int J. Med. Sci.* 2012; 9(2):157-62;

Dellinger R P, Levy M M, Rhodes A, Annane D, Gerlach H, Opal S M, Sevransky J E, Sprung C L, Douglas I S, Jaeschke R, Osborn™, Nunnally M E, Townsend S R, Reinhart K, Kleinpell R M, Angus D C, Deutschman C S, Machado F R, Rubenfeld G D, Webb S A, Beale R J, Vincent J L, Moreno R; Surviving Sepsis Campaign Guidelines Committee including the Pediatric Subgroup. Surviving sepsis campaign: international guidelines for management of severe sepsis and septic shock: 2012. *Crit. Care Med.* 2013 February; 41(2):580-637;

Feng, Z., Wang, Y., Qi, W., "The small intestine, an underestimated site of SARS-CoV-2 infection: from Red Queen Effect to probiotics", Preprints 2020, 2020030161;

Finnegan, C M., Rawat, S S., Puri, A., Wang, J M., Ruscetti, F W., Blumenthal, R., "Ceramide, a target for antiretroviral therapy", 2004, *Proc. Natl. Acad. Sci. USA* 101:15452-15457;

Green, S J., Scheller, L F., Marletta, M A., Seguin, M C., Klotz, F W., Slayter, M., Nelson, B J. e Nacy, C A., "Nitric oxide: cytokine regulation of nitric oxide in host resistance to intracellular pathogens", 1994, Immunol. Lett. 43:87-94;

Huang, C., Wang, Y., Li, X et al., "Clinical features of patients infected with 2019 novel coronavirus in Wuhan, China", 2020, *Lancet* 395:497-506;

Laviolette, L., Laveneziana, P, ERS Research Seminar Faculty, "Dyspnoea: a multidimensional and multidisciplinary approach", giu. 2014, *Eur. Respir. J.* 43(6): 1750-62;

Lew, L C., Liong, M T., "Bioactives from probiotics for dermal health: functions and benefits", 2013, *J. Appl. Microbiol.* 114(5):1241-1253;

Leyer, G J., Shuguang, Li, Mohamed E. Mubasher, Cheryl Reifer, Arthur C. Ouwehand, "Probiotic effects on cold and influenza-like symptom incidence and duration in children", ago. 2009, *Pediatrics* 124(2):e172-e179;

Peiris, J S M., Chu, C M., Cheng, V C C. et al., "Clinical progression and viral load in a community outbreak or coronavirus-associated SARS pneumonia: a prospective study", 2003, *Lancet* 361:1767-1772;

Pritzl, C J., Seo, Y-J., Xia, C., Vijayan, M., Stokes Z D., Hahm, B., "A ceramide analogue stimulates dendritic cells to promote T cell responses upon virus infections", 2015, *J. Immunol.* 194:4339-4349;

Prompetchara, E., Ketloy, C., Palaga, T., "Immune responses in COVID-19 and potential vaccines: Lessons learned from SARS and MERS epidemic", 27 Feb. 2020, Asian Pac. *J. Allergy Immunol.* 38(1):1-9;

Schloer S, Brunotte L, Goretzko J, Mecate-Zambrano A, Korthals N, Gerke V, Ludwig S, Rescher U. "Targeting the endo-lysosomal host-SARS-CoV-2 interface by clinically licensed functional inhibitors of acid sphingomyelinase (FIASMA) including the anti-depressant fluoxetine", Emerg. Microbes Infect. 2020 December; 9(1):2245-2255.

Tian, S., Hu, W., Niu, L., Liu, H., Xu, H., Xiao, S-Y., "Pulmonary pathology of early phase 2019 novel coronavirus (COVID-19) pneumonia in two patients with lung cancer", 2020, *Journal of Thoracic Oncology;*

Tian, Y., Jennings, J., Gong, Y., Sang, Y., "Viral infections and interferons in the development of obesity", 2019, *Biomolecules* 9(11):726;

The GLIMMIX procedure. SAS/STAT User's Guide. 2009, Version9.2,

Xu, Z., Shi, L., Wang, Y., Zhang, J., Huang, L., Zhang, C. et al., "Pathological findings of COVID-19 associated with acute respiratory distress syndrome", 2020, *The Lancet Respiratory Medicine* 8(4):420-422;

Ye, Z., et al. "Chest C T manifestations of new coronavirus disease 2019 (COVID-19): a pictorial review", 2020, *Eur. Radiol.*

24

The invention claimed is:

1. A method for treating COVID-19 caused by SARS-CoV-2, or for treating a respiratory failure induced or aggravated by a SARS-CoV-2 viral infection, in an individual in need thereof, the method comprising administering to the individual in need thereof a formulation comprising a bacterial composition or bacterial compositions comprising:

1% to 70% by weight of *Streptococcus thermophilus* DSM32245,

1% to 20% by weight of *Lactobacillus acidophilus* DSM32241,

1% to 20% by weight of *Lactobacillus helveticus* DSM32242,

1% to 20% by weight of *Lactobacillus paracasei* DSM32243,

1% to 30% by weight of *Lactobacillus plantarum* DSM32244,

1% to 70% by weight of *Lactobacillus brevis* DSM27961, and

1% to 40% by weight of *Bifidobacterium animalis* subsp. *lactis* DSM32246, and *Bifidobacterium animalis* subsp. *lactis* DSM32247, wherein the bacterial composition or bacterial compositions have: (a) an arginine deiminase activity of 120 µmol L-citrulline/h/g of composition, wherein said activity comprises inhibition of nitric oxide synthase by conversion of L-arginine to L-citrulline; and, (b) a sphingomyelinase activity comprising generation of 90 nmol ceramides/h/g of composition.

2. The method of claim 1, wherein the bacterial composition or bacterial compositions are formulated for oral administration and are orally administered.

3. The method of claim 2, wherein the bacterial composition or bacterial compositions have a concentration of bacteria of between about 50 billion to 8,000 billion bacteria per gram.

4. The method of claim 1, wherein the bacterial composition or compositions are inserted into or on a face mask or a Non Invasive Ventilation (NIV) device.

5. The method of claim 1, wherein the bacterial composition or bacterial compositions are formulated for administration via an airway, and the bacterial composition or compositions are administered via the airway by inhalation or insufflation.

6. The method of claim 5, wherein the bacterial composition or bacterial compositions are formulated and administered as an aerosol, an insufflation fluid or a powder comprising saline or purified water.

7. The method of claim 5, wherein the bacterial composition or bacterial compositions are formulated and administered as a fluid or a powder by an aerosol or insufflation.

8. The method of claim 6, wherein the aerosol or insufflation fluid or powder compositions have a bacteria concentration of between about 100,000 to 50 billion bacteria per gram.

9. The method of claim 5, wherein the bacterial composition or bacterial compositions are formulated and administered as nasal drops having a concentration of bacteria of between about 100,000 to 800 billion bacteria per gram.

10. The method of claim 1, wherein the bacterial composition or bacterial compositions are formulated and administered orally, buccally or rectally as a lipogel, and the bacterial composition or compositions have a concentration of bacteria of between about 1 billion to 800 billion bacteria per gram.

11. The method of claim 1, further comprising treating the individual with an oxygen therapy or ozone therapy.

12. The method of claim 1, wherein bacteria in the bacterial composition or bacterial compositions are viable, non-viable, sonicated, tindalised or lyophilised.

13. The method of claim 1, wherein the bacterial composition or bacterial compositions are formulated with at least one pharmaceutically acceptable excipient.

14. The method of claim 1, wherein the bacterial composition or bacterial compositions are formulated and administered in the form of a powder, a capsule, a granule or a lipogel.

15. The method of claim 5, wherein the bacterial composition or bacterial compositions are formulated and administered as a powder, a solution, a suspension, a dispersion spray, an aerosol fluid, a nasal drop or an aerosol fluid.

\*    \*    \*    \*    \*